United States Patent [19]

Huang et al.

[11] Patent Number: 5,232,948
[45] Date of Patent: Aug. 3, 1993

[54] SUBSTITUTED MONOCYCLIC ARYL COMPOUNDS EXHIBITING SELECTIVE LEUKOTRIENE B₄ ANTAGONIST ACTIVITY

[75] Inventors: Fu-Chih Huang, Gwynedd; Wan K. Chan, Wayne; Charles A. Sutherland, Greenlane; Robert A. Galemmo, Jr., Collegeville; Michael N. Chang, Newtown, all of Pa.

[73] Assignee: Rhone-Poulenc Rorer Pharmaceuticals Inc., Collegeville, Pa.

[21] Appl. No.: 580,227

[22] Filed: Sep. 10, 1990

[51] Int. Cl.⁵ .................... A61K 31/19; C07C 229/34
[52] U.S. Cl. .................... 514/563; 514/562; 514/381; 514/538; 514/539; 562/442; 562/426; 562/443; 562/451; 560/42; 560/37; 548/253; 548/251

[58] Field of Search .............. 562/443, 451, 422, 466; 560/42, 37; 514/533, 538, 539, 563, 564, 381; 548/253, 251

[56] References Cited

U.S. PATENT DOCUMENTS 3,828,095  8/1974  Boschetti ........................... 562/451
4,460,580  7/1984  Ostermayer et al. ............... 514/620
4,497,813  2/1985  Ostermayer et al. ............... 514/166

FOREIGN PATENT DOCUMENTS 41491    12/1981  European Pat. Off. ............ 560/42
2139626   9/1972  Fed. Rep. of Germany ....... 560/42

OTHER PUBLICATIONS

F. Ostermayer et al. (IV), *Chemical Abstracts* 93:P220465r, p. 502, (1980) English abstract of E.P. patent 5,848.

F. Ostermayer et al. (III), *Chemical Abstracts* 94:121135x, p. 660 (1981) English abstract of E.P. patent 15,505.

*Primary Examiner*—Richard L. Raymond
*Assistant Examiner*—Mark W. Russell
*Attorney, Agent, or Firm*—James A. Nicholson; Marin F. Savitzky

[57] ABSTRACT

Monocyclic aryl compounds having selective LTB₄ antagonists properties and comprising an amido substituent, a substituent group having a terminal carboxylic acid or derivative thereof and a lipophilic substituent, therapeutic compositions and methods of treatment of disorders which result from LTB₄ activity using the monocyclic aryl compounds are disclosed.

12 Claims, No Drawings

SUBSTITUTED MONOCYCLIC ARYL COMPOUNDS EXHIBITING SELECTIVE LEUKOTRIENE B4 ANTAGONIST ACTIVITY

FIELD OF THE INVENTION

The present invention relates to a class of novel compounds useful in the treatment of a variety of diseases that involve undesirable inflammatory or hypersensitivity responses in diverse animal tissues. Approaches to the treatment of these responses have been as varied as the tissues in which such responses take place, and include the administration of antihistamines, analgesics such as aspirin, topical coal tar as well as others.

A more recent approach to the moderation of inflammatory and hypersensitivity responses has focused on blocking the action of arachidonic acid metabolites (including the prostaglandins), lipoxygenases and the leukotrienes. The leukotrienes (LT) metabolites are formed by oxygenation of a lipoxygenase (5-hydroperoxytetraenoic acid (5-HPETE)) which is formed by the specific oxygenation of the C-5 position of arachidonic acid. The first leukotriene formed in the metabolic pathway is the unstable epoxide intermediate leukotriene $A_4$ ($LTA_4$) which is the precursor to the family of peptido-leukotrienes, the first in the pathway being $LTC_4$ which is formed by glutathione addition. $LTC_4$ is transformed subsequently into $LTD_4$ and $LTE_4$ by successive elimination of a glutamyl and glycine residue. The peptido-leukotrienes primarily act on smooth muscle and other cells having contractile capacity, as well as playing a key role in hypersensitivity reactions. In addition, the peptidoleukotrienes are spasmogens, increase vascular permeability, activate airway smooth muscle, stimulate mucous secretion and are involved with the pathogenesis of certain inflammatory diseases such as bronchitis, ectopic and atopic eczema and psoriasis. Leukotrienes appear to be involved in the pathogenesis of asthma such as allergic pulmonary disorders of asthma, hay fever and allergic rhinitis. In addition, $LTC_4$, $LTD_4$ and $LTE_4$ may also decrease blood pressure by an action on the heart, because they reduce myocardial contractility and coronary blood flow.

Another family of leukotrienes, $LTB_4$, is derived from $LTA_4$ by hydrolase-catalyzed addition of water. This 5,12-dihydroxy derivative causes adhesion and chemotactic movement of leukocytes, stimulates aggregation, enzyme release and generation of superoxide in neutrophils. Additionally, $LTB_4$ is a potent chemotactic and chemokinetic agent for eosinophils, macrophages and monocytes, stimulates suppressor T lymphocytes and enhances natural cytotoxic cell activity. $LTB_4$ is also a potent (indirect) bronchoconstrictor but in contrast to the peptidoeukotrienes $C_4$, $D_4$ and $E_4$ does not appreciably stimulate mucous production and induce edema of the airways by increasing vascular permeability.

REPORTED DEVELOPMENTS

It has been suggested that compounds antagonizing $LTB_4$ activity may be valuable in the treatment of inflammatory diseases caused by tissue degrading enzymes and reactive chemicals liberated by tissue-infiltrating and aggregating polymorphonuclear leukocytes. Such disease states include inflammatory bowel disease, reperfusion injury, chronic lung diseases, various arthritic conditions, inflammatory conditions associated with asthma (such as late phase hypersensitivity) and psoriasis.

The literature reports a variety of compounds exhibiting leukotriene $B_4$ antagonist activity. These include compounds having chemical structures mimicking leukotriene structures such as Sumitomo's SM 9064, UpJohn's U-75360 and U-75302 and Ciba Geigy's CGS 23113. Other compounds, some of which include monocyclic ring structures and which are disclosed in EP 276064, EP 276065 and EP 292977, are reported to exhibit both $LTD_4$ and $LTB_4$ antagonist properties.

The present invention is directed to a class of novel monocyclic ring containing compounds which exhibit selective $LTB_4$ antagonist activity.

SUMMARY OF THE INVENTION

This invention relates to compounds having $LTB_4$ antagonist properties and to therapeutic compositions and methods for the treatment of disorders which result from $LTB_4$ activity. In general, this invention comprises monocyclic aryl compounds having selective $LTB_4$ antagonist properties and comprising an amido substituent, a substituent group having a terminal carboxylic acid or derivative thereof and a lipophilic substituent.

DETAILED DESCRIPTION AND PREFERRED EMBODIMENTS

As employed above and throughout this disclosure, the following terms, unless otherwise indicated, shall be understood to have the following meanings:

"Bicyclic aryl" means a bicyclic ring system composed of two fused rings which may be a partially or completely unsaturated carbocyclic and/or heterocyclic ring. Preferred bicycles include naphthalene, indole, benzothiophene, benzofuran, quinoline, chromone and purine.

"Monocyclic aryl" means a partially or completely unsaturated carbocyclic or heterocyclic ring having 1–3 hetero atoms selected from nitrogen, oxygen and sulfur. Preferred monocycles include benzene, thiophene, pyridine, furan and pyrimidine.

"Aryl" refers to a partially or completely unsaturated carbocyclic or heterocyclic aromatic ring. Preferred aryl is phenyl.

"Alkyl", either alone or with various substituents defined herein, means a saturated aliphatic hydrocarbon, either branched- or straight-chained. A "loweralkyl" is preferred having about 1 to about 6 carbon atoms. Examples of alkyl include methyl, ethyl, n-propyl, isopropyl, butyl, sec-butyl, t-butyl, amyl and hexyl.

"Alkoxy" refers to a loweralkyl-O-group.

"Alkylthio" refers to a loweralkyl-S-group.

"Alkenyl" refers to a hydrocarbon having at least one point of unsaturation and may be branched- or straight-chained. Preferred alkenyl groups have 2 to about 6 carbon atoms present. Exemplary alkenyl groups include vinyl, allyl, ethynyl and isopropenyl.

The preferred aryloxy group is phenoxy.

"Aralkyl" means an alkyl group substituted by an aryl radical. The preferred aralkyl groups are benzyl or phenethyl.

The preferred aralkoxy groups are benzyloxy and phenethoxy.

The preferred aralkylthio group is benzylthio.

"Halo" means a halogen. Preferred halogens include chloride, bromide and fluoride. The preferred haloalkyl group is trifluoromethyl.

More specifically, the monocyclic aryl ring compounds are described by formula I:

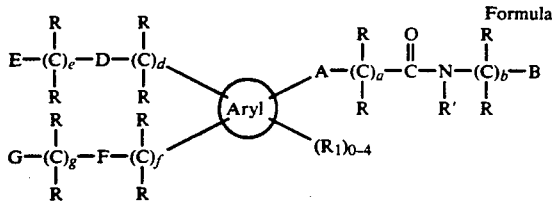

where: Aryl is a monocyclic ring of about 5 to about 7 atoms which may be partially or completely unsaturated carbocyclic or heterocyclic of 1-3 hetero atoms said hetero atoms are not vicinal oxygen and/or sulfur atoms.

Preferred aryl rings include pyrrole, thiophene, furan, cyclopentadien, imidazole, pyrazole, 1,2,4-triazole, pyridine, pyrazine, pyrimidine, pyradazine, isothiazole, isoxazole, s-triazine and benzene.

Turning now to the three substituents which are necessarily attached to the monocyclic ring, the preferred first substituent, which we have called the amido function, may be described by formula II:

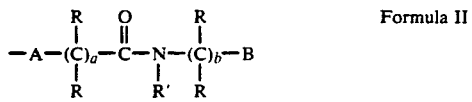

The preferred second substituent having a terminal carboxylic acid or derivative thereof may be described by formula III:

The preferred third substituent, the lipophilic substituent, may be described by formula IV:

where A, B, D, E, F, G, R, R', a, b, d, e, f and g are as described below.

These above substituents of formulae II to IV may be attached at various positions of the aryl ring.

The remaining positions on the aryl ring, if available, may be substituted by $R_1$. This is described below. In the case of those compounds having an available protonated nitrogen atom in the ring, this also may be substituted by one of the substituents of Formulae II–IV or substituted by R' which is also described below.

The following definitions apply to the substituents of formulae I to IV, each of which is attached at a suitable position on the aryl ring, where:

A is —CRR, O, S, NR', SO or $SO_2$;

B and G are each independently a substituted or unsubstituted monocyclic or bicyclic aryl ring;

D and F are each independently O, S, NR', SO, $SO_2$, CONR', NR'CO, —CRR, $(CR=CR)_x$ where x is 0–2 or C≡C;

E is —COOR', —CONR'R',

where y is 2–5, —CN, $CONHSO_2R$,

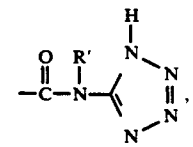

tetrazolyl or substituted tetrazolyl where the substituents are alkyl, carboxyalkyl or carbalkoxyalkyl;

R is independently hydrogen or —$(CH_2)_m$—$R_1$ where m is 0–5 or together with a vicinal R group or vicinal R' group forms a 4–7 membered ring;

R' is hydrogen, alkyl or aralkyl;

a, b, d, e, f and g are 0–3 provided $d+f+g+x \neq 0$;

$R_1$ is hydrogen, alkyl, alkenyl, phenyl, aralkyl, alkoxy, aryloxy, aralkoxy, amino, mono- and dialkylamino, mercapto, alkylthio, aralkylthio, nitro, halo or haloalkyl.

Preferred compounds of this invention are described by those compounds of formula V:

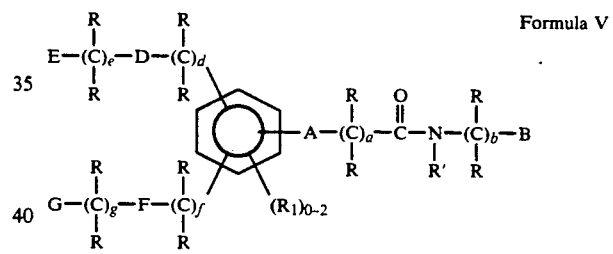

where:

A is —CRR or O;

B and G are independently phenyl or substituted phenyl and B and/or G may be substituted with 1 to about 3 R" groups where R" is alkyl, haloalkyl, alkoxy, halo or nitro;

D is a chemical bond, O, —CRR or $—(CR=CR)_x$ where x is 1 or 2;

E is, —COOR', —CONR'R',

where y is 2–5, —CN, —$CONHSO_2R'$,

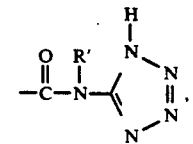

tetrazolyl or substituted tetrazolyl where the substituent is alkyl, carboxyalkyl or carbalkoxyalkyl;

F is O or —CRR;

R is hydrogen or —(CH$_2$)$_m$—R$_1$ where m is 0-5 or together with a vicinal R group or vicinal R' group forms a 4-7 membered ring;

R$_1$ is hydrogen, alkyl, alkenyl, phenyl, alkoxy, amino, mono- and di-alkylamino, mercapto, alkylthio, halo or haloalkyl;

R' is hydrogen, alkyl or aralkyl; and a, b, d, e, f and g are independently 0–3.

The preferred positions for substitution in the molecule of formula V are the 1, 3 and 5 positions.

The more preferred compounds include those where:

A is CHR or O;

B and G are phenyl or substituted phenyl where the substituents are loweralkyl or loweralkoxy;

D is a bond, O, —CHR or (CR=CR)$_x$ where x is 1 or 2;

E is —COOR' or tetrazolyl;

F is O or —CHR;

R is hydrogen, loweralkyl or together with a vicinal R group or vicinal R' group forms a 4-7 membered ring;

R' is hydrogen, loweralkyl or lowerarakyl; and a, b, d, e, f and g are independently 0–3.

Among the most preferred amido substituents are:

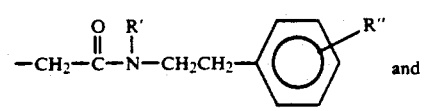

and

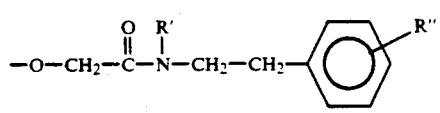

where R' is hydrogen or lower alkyl and R" is hydrogen, lower alkyl or lower alkoxy.

Among the most preferred terminal acidic substituents are: —(CRR)$_d$—E where d is 0–4, —(CR=CR)$_x$—E where x is 1-2, —O—(CRR)$_d$—E where d is 1-3, —O—(CRR)$_d$—CR=CR—E where d is 1-3 and R is hydrogen or lower alkyl and E is —COOH or

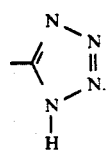

Among the most preferred lipophilic substituents are:

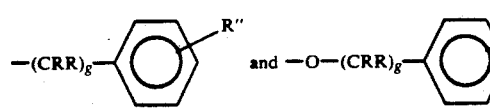

where g is 0–3 and R is hydrogen or lower alkyl and R" is hydrogen, lower alkyl or lower alkoxy. In those special embodiment cases where the lipophilic substituent is attached to a substituent containing the amido or carboxylic acid or derivative function, then g may also be 0.

While this invention necessitates the presence of three specific substituents be present on the aryl ring as described by formulae I and V, it is often desirable to have a another substituent present. This also may be the same or different as those of formulae II-IV already present. Other substituents of R$_1$ may likewise be desired. It is to be understood that such compounds fall within the scope of this invention.

It may be of interest to one skilled in the art that compounds where E is OR' may also be of value as LTB$_4$ antagonists.

The compounds of this invention may be prepared by employing art recognized procedures from known compounds or readily preparable intermediates. Exemplary general procedures are as follows.

Since the compounds of this invention have three substituents which are necessarily present, the introduction of each substituent to the aryl ring system is, of course, dependent on the specific substituents involved and the chemistry necessary for their formation. Thus, consideration of how one substituent would be affected by a chemical reaction when forming a second substituent would involve techniques familiar to the skilled artisan. This would further be dependent on the ring involved.

It is convenient to synthesize these molecules by employing condensation reactions at reactive A, D and F cites of the molecule. Exemplary general procedures are as follows and are shown for convenience using the benzene ring system. Of course, while the following reactions involved are basic to developing substituted phenyl molecules having the three required substituents present, the substitution patterns for other monocyclic rings would depend on the chemistry of the particular ring. Any such adjustments to the chemistry would be familiar to one skilled in the art.

Thus, in order to prepare those compounds where A, D or F is O, S or NR' the following reactions or combination of reactions may be employed:

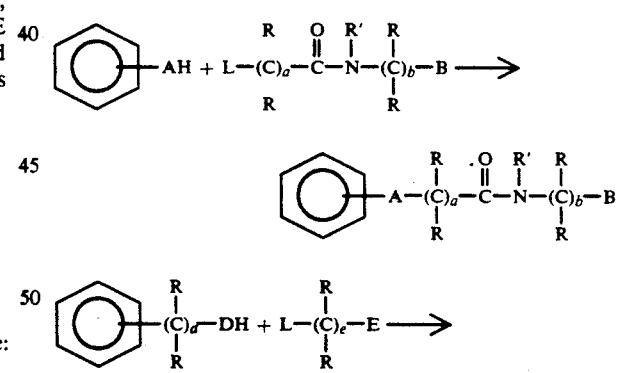

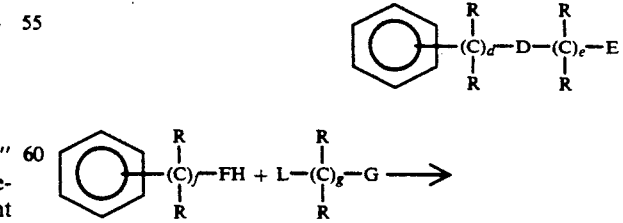

When A, D or F is O or S, the compounds may be prepared by condensation of the aryl alcohol or thiol with a compound of the formulae

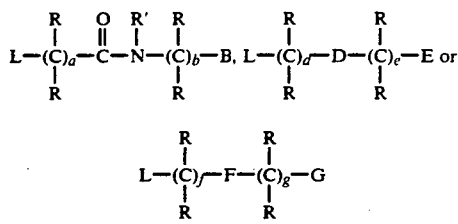

where E is preferably a nitrile, ester or tetrazole and L is a leaving group such as halo, tosylate or mesylate. This reaction is usually carried out in the presence of any base normally employed to deprotonate an alcohol or thiol such as sodium hydride, sodium hydroxide, triethyl amine, sodium bicarbonate, diisopropylethylamine or methyl magnesium halides.

Reaction temperatures are in the range of room temperature to reflux and reaction times may vary from 2 to 96 hours. The reaction is usually carried out in a solvent that will dissolve both reactants and is inert to both as well. Solvents include, but are not limited to diethyl ether, THF, N,N-dimethylformamide, dimethylsulfoxide, dioxane and the like.

When A is an alkyl group, it is convenient to prepare these compounds by Friedel-Crafts alkylation or by the Wittig reaction followed by reduction.

In the case where A, D or F is SO or $SO_2$, then treatment of the thio compound with m-chlorobenzoic acid or sodium periodate results in the sulfinyl compound. Preparation of the sulfonyl compound may be accomplished by known procedures such as dissolving the sulfinyl compound in acetic acid and treating with 30% $H_2O_2$.

Those compounds where F and/or D are

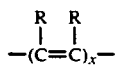

where x is 1 or 2, are prepared by reacting the appropriate aldehyde or ketone with an appropriate Wittig reagent or modified Wittig reagent of the formula

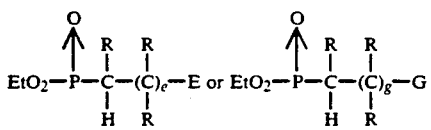

where E is cyano or carbalkoxy. Thus for example

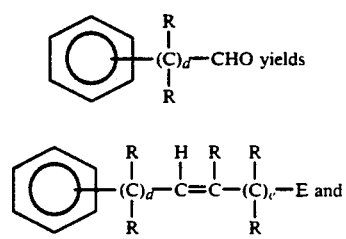

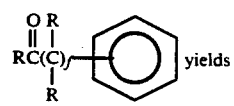 yields

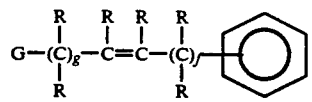.

Reference for the Wittig reaction and modified Wittig reaction to control the formation of the trans and cis configuration at the double bond and the isomerization of cis and trans isomers can be found in A. Maercher, *Organic Reactions*, 14, 270,1965.

The intermediate aldehyde compounds may be prepared in the usual manner from the corresponding carboxylic acid with an alkyllithium reagent, or from the oxidation of the corresponding alcohol. The aldehyde can also be obtained by Friedel-Crafts acylation or formylation ($POCl_3$/DMF) of the aryl ring.

When F and/or D are

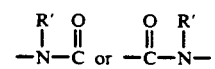

then the condensation of an acid or an acid halide with the appropriate aryl amine will give the desired compound.

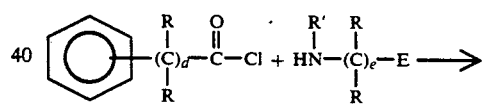

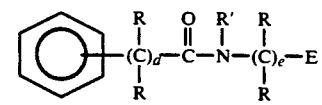

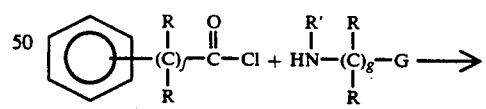

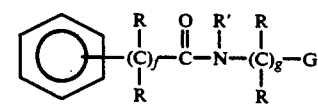

The tetrazoles may be formed from the nitrile at various stages of the synthesis by treatment with hydrazoic acid formed in situ from sodium azide and an acid. The nitrile may also be converted to the acids, esters or amides by known methods.

It is convenient to develop the synthesis of the final product by successively forming each desired substituent in turn. Thus in order to prepare a compound

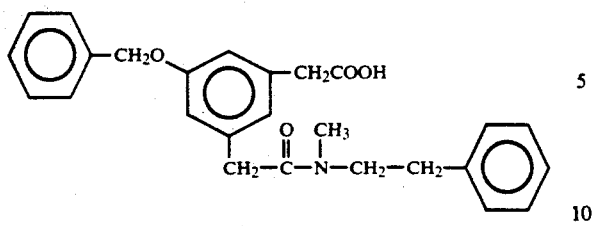
A further example may be described in the preparation of the following compounds which may exist as the cis or trans stereoisomers or their racemic mixture:
the following reaction sequence could be used:
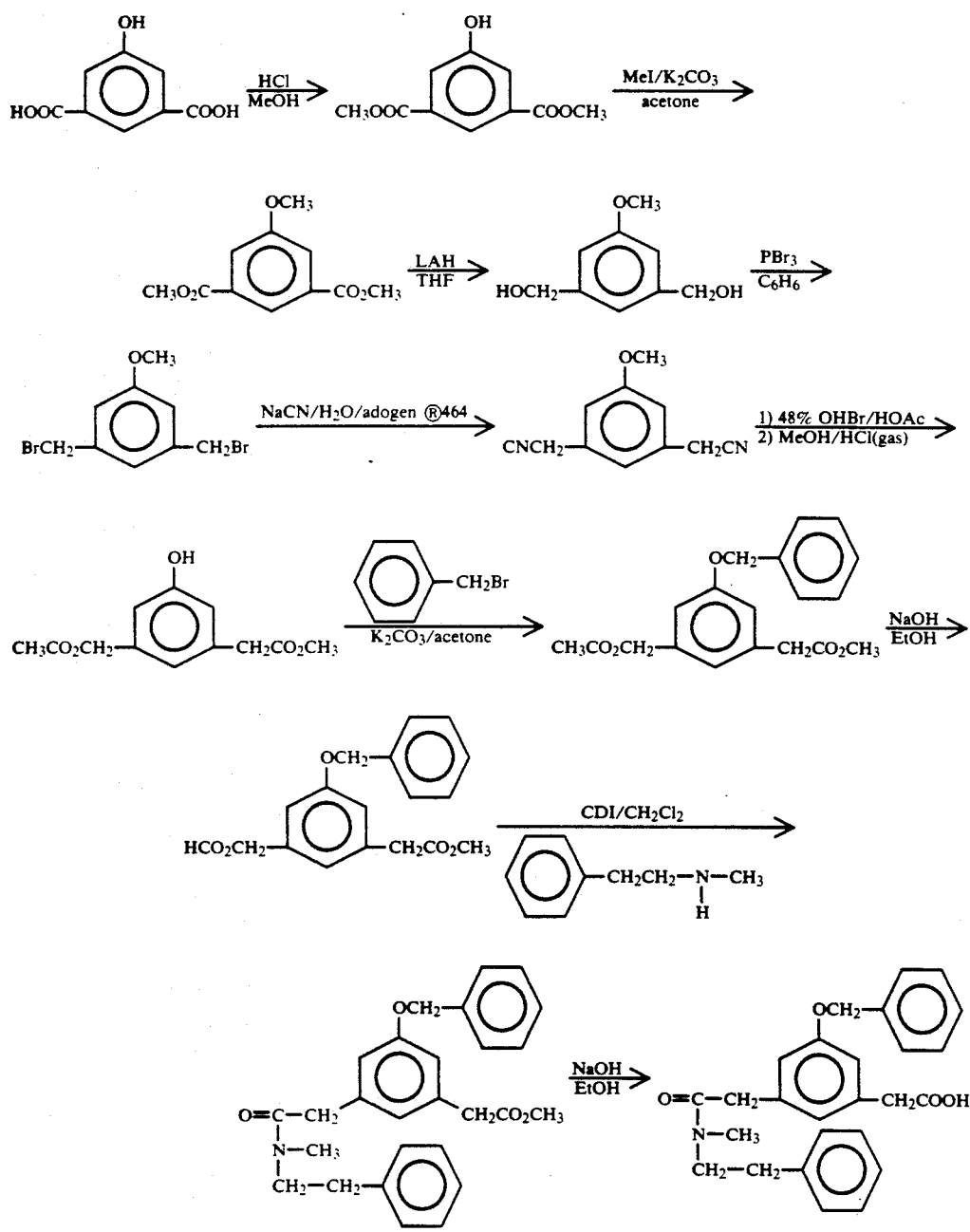

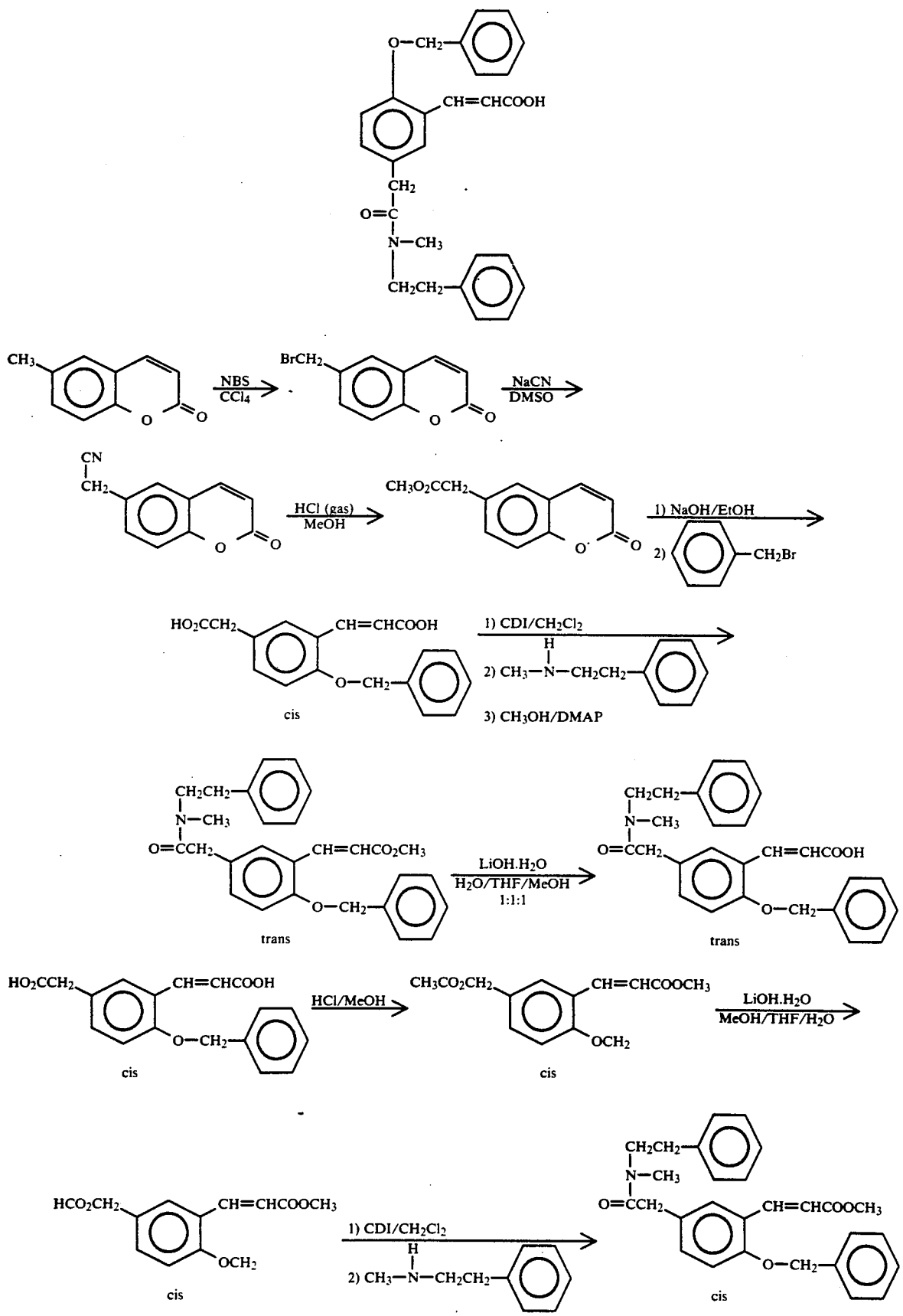

-continued

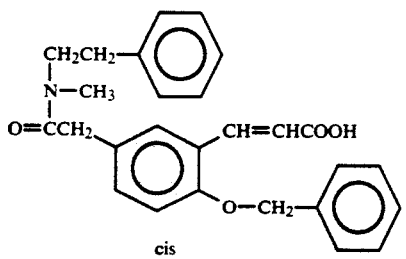

cis

Certain compounds of this invention may have at least one asymmetric carbon atom such as those compounds having different geminal R groups or those compounds which contain an asymmetric carbon atom. Further, certain compounds of this invention may exist in their cis or trans configuration such as those compounds where D and/or F is CR=CR. As a result, those compounds of this invention may be obtained either as racemic mixtures, diastereoisomeric mixtures or as individual enantiomers. When two or three asymmetric centers are present the product may exist as mixtures of two or four diastereomers. Of course it is understood that certain other compounds within the scope of this invention could have a number of stereocenters. In general, a compound with x stereocenters can have a maximum of $2^x$ stereoisomers. Therefore, a compound having three such centers gives rise to a maximum of eight stereoisomers, while one having four produces sixteen, etc. The product may be synthesized as a mixture of the isomers and then the desired isomer separated by conventional techniques such as chromatography or fractional crystallization from which each diastereomer may be resolved. On the other hand, synthesis may be carried out by known stereospecific processes using the desired form of the intermediate which would result in obtaining the desired stereospecificity.

Reference to the separation of cis and trans isomers by chromatography may be found in W. K. Chan, et al, J. Am. Chem. Soc. 96, 3642, 1974.

It is to be understood that the scope of this invention encompasses not only the various isomers which may exist but also the various mixture of isomers which may be formed.

The resolution of the compounds of this invention and their starting materials may be carried out by known procedures. Incorporation by reference is hereby made to the four volume compendium *Optical Resolution Procedures for Chemical Compounds:* Optical Resolution Information Center, Manhattan College, Riverdale, N.Y. Such procedures are useful in the practive of this invention. A further useful reference is *Enantiomers. Racemates and Resolutions:* Jean Jacques, Andre Collet and Samuel H. Wilen; John Wiley & Sons, Inc., New York, 1981. Basically, the resolution of the compounds is based on the differences in the physical properties of diastereomers. Conversion of the racemates into a mixture of diastereomers by attachment of an enantiomerically pure moiety results in forms that are separable by fractional crystallization, distillation or chromatography.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, maleic, tartaric and the like which are pharmaceutically acceptable. Basic salts for pharmaceutical use are the Na, K, Ca and Mg salts.

Various substituents on the present new compounds, e.g., as defined in $R_1$ and $R''$ can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added by nitration and the nitro group converted to other groups, such as amino by reduction, and halo by diazotization of the amino group and replacement of the diazo group. Acyl groups can be added by Friedel-Crafts acylation. The acyl groups can then by transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

Compounds within the scope of the present invention have potent activity as leukotriene $B_4$ antagonists and as such possess therapeutic value in the treatment of inflammatory conditions and hypersensitivity responses. $LTB_4$ is implicated in diseases such as rheumatoid arthritis, gout, psoriasis and inflammatory bowel disease and therefore compounds which demonstrate $LTB_4$ antagonist properties would be of value in the control of these states.

The $LTB_4$ guinea pig polymorphonuclear membrane binding assay can be used to determine compounds exhibiting $LTB_4$ receptor antagonist properties. Compounds active in this assay can then be subjected to the guinea pig peritoneal PMN $LTB_4$-induced aggregation assay. THE $LTB_4$-induced aggregation assay determines the functional activity of a compound. The guinea pig $LTB_4$-induced wheal assay is used to determine in vitro activity.

Assay for Inhibitors of ($^3$H)-LTB$_4$ Binding to Membranes From Guinea Pig Polymorphonuclear Leukocytes

Preparation of Test Compounds

Dissolve compounds to a concentration 100-fold higher than the highest desired concentration for testing. Serially dilute the compound so that all dilutions are 100-fold higher than the assay concentration desired. Compounds are typically dissolved in DMSO. If compounds are insoluble in DMSO, solutions are heated or sonicated to induce solubilization. Compounds may also be dissolved in ethanol.

Final assay concentrations of DMSO and ethanol can be as high as 1.0% and 2.0% (v/v); these concentrations have no measurable effects on specific binding.

Preparation of the Membrane Receptor Fraction

To obtain polymorphonuclear leukocytes (PMNs), 25-30 male Hartley guinea pigs (250-350 g) are intraperitoneally injected with 6 mls of an 8% sodium caseinate solution. 18 to 24 hours later, the guinea pigs are sacrificed by decapitation. The peritoneal cavity is lavaged with 15 mls of isolation buffer. The cells are collected and centrifuged at 200 xg for 10 minutes. Contaminating red blood cells can be removed by hypotonic lysis. The cells are resuspended in isolation buffer and centrifuged as before. They are filtered through gauze and centrifuged again. The resulting pellet is suspended in 3 ml of sonication buffer, counted and brought to a concentration of $1 \times 10^8$ cells/ml. This suspension is lysed on ice with 5 bursts of 30 seconds separated by 1 minute intervals. The homogenate is centrifuged at 200 xg for 10 minutes at 4° C. Aliquots of supernatant are transferred to high speed centrifuge tubes (1 tube per 3 guinea pigs). The tubes are centrifuged at 49,000 xg for 15 minutes at 4° C. The pellets are resuspended by three 5 second bursts of sonication, separated by 20 second intervals. This suspension is centrifuged at 50,000 xg for 20 minutes at 4° C. Pellets are stored at $-70°$ C. for up to 3 months.

To use in the binding assay, the pellet is thawed at room temperature and suspended in 9 mls of assay buffer (sonication may be necessary).

Binding Assay

Each assay tube (16×100 mm) contains the following:
- 345 µl Assay Buffer
- 5 µl Test compound or solvent
- 50 µl $^3$H-LTB$_4$ (0.50 nM)
- 100 µl Protein preparation (0.2 mg)

Incubations are done at 30° C. for 40 minutes in a water bath. Reactions are started by the addition of ($^3$H)-LTB$_4$ solution. Samples are collected via a Brandel M24 Harvester for binding assays. Tubes should be washed with a total of 19 ml cold wash buffer.

The filters are transferred to 7 ml plastic scintillation vials to which 6.0 ml of appropriate scintillation fluid (e.g., Scintiverse®) is added. After being allowed to equilibrate for 12 hours, the radioactivity is counted with a liquid scintillation counter appropriately set for tritium.

The required control assay tubes include the following:
(a) Total Binding: No test compound is added; buffer is substituted.
(b) Non-Specific Binding: Non-labeled ligand is added at a concentration of 1 µM.
(c) Solvent Controls: If test compound is dissolved in a solvent, controls for both Total Binding and Non-Specific Binding containing solvent but no compounds are required.

Calculations

Specific binding is defined as that amount of radioligand prevented from binding by 1000-fold excess non-labeled ligand, i.e., total binding minus non-specific binding. This operational definition is verified by Scatchard analysis of total binding.

Inhibition of specific binding is defined as the decrease in specific binding caused by the test compound, $$\frac{SB_C - SB_T}{SB_C} \times 100$$

where $SB_C$ is the specific binding in the absence of test compound and $SB_t$ is the specific binding in the presence of test compound. The $I_{50}$ values (concentrations required to inhibit specific binding by 50%) are determined by graphic analysis of the specific binding observed in the presence of various concentrations of test compound.

The results of this test indicate that compounds of this invention exhibit valuable LTB$_4$ receptor binding properties which are useful in the treatment of inflammatory conditions and hypersensitivity responses.

LTB$_4$-Induced Wheal Formation in Guinea Pig

LTB$_4$ plays the role of a mediator in cellular induced inflammation. The induction of chemokinesis and chemotaxis of PMNs and macrophage by LTB$_4$ have contributed to its association with the vascular aspects of acute inflammatory reactions.

In this test intradermal injection of 0.1 ml of a 10 µg/ml solution of LTB$_4$ to guinea pig back skin causes the formation of a wheal. This wheal is visualized by the prior intravenous injection with the indicator 1% Evan's Blue dye. Following a 2 hour incubation post-LTB$_4$ challenge, the guinea pigs are euthanized via $CO_2$ asphyxiation. Their dorsal skins are reflected and the diameters of the challenged sites are compared with those of the vehicle control injected sites.

Preparation and Handling of Guinea Pigs

The guinea pigs must be quarantined 5 to 7 days prior to the study. The day before the test, the back and hind limbs are shaved taking care not to nick the skin. After shaving, the guinea pigs are fasted, but water is provided.

On the day of the test, the guinea pigs are weighed and identified with an ink mark designating them with numbers 1 through 5 in each group. Groups are formed by random distribution.

Preparation and Route of Administration of Compounds

The oral vehicles are Polyethylene Glycol (PEG 400) (2 ml/kg) and methocel (0.5% w/v) (10 ml/kg). Exposure to the ultrasound of a Branson sonicator assures uniformity of suspension or dissolution of the test compounds. Compounds for parenteral administration are dissolved in saline with the assistance of 0.1N HCl and 0.1N NaOH and then adjusting the pH to near neutrality.

Although test compounds are usually administered orally, other routes of administration such as intravenous, intraperitoneal or subcutaneous may be used.

Preparation of Leukotriene B₄ for Intradermal Infection

LTB₄ is obtained as a stock solution (50 μg/ml) ethanol and is stored at −80° C. until required for use. The stock solution or an appropriate aliquot is transferred from the ampule into a 10 ml glass vial using a pasteur pipette. The stock solution is then evaporated to dryness under a slow, steady stream of argon gas.

A solution of freshly prepared 0.25% Bovine Albumin in Phosphate-Buffered Saline is bubbled with argon gas until the saturation point is reached (approximately 5 minutes). This argon-saturated vehicle is then used to reconstitute the evaporated LTB₄ stock residue to yield a final working concentration of 10 μg/ml. The rubber stoppered vial of LTB₄ working solution is kept on wet ice during the study.

Preparation of Evan's Blue Dye Solution

Because Evan's Blue is an easily visible marker that binds to the plasma proteins, it has been selected to assist the investigator in the measurement of the wheals induced during the study. Evan's Blue Dye is dissolved as a 1% w/v solution in 0.9% w/v physiologic saline. The number of 1 ml plastic disposable syringes, fitted with 27 gauge, ½ inch needles and filled with the 1% dye solution, is determined by the number of animals expected to be included in the study.

Conduct of an Experiment

Test compounds or their appropriate controls are administered orally with 16 gauge, 3 inch dosing cannulas. Immediately after dosing, the guinea pig is injected intravenously with 1 ml of 1% Evan's Blue Dye into a digital vein in the left or right shaved hind limb. This injection is facilitated best through the use of a 1 ml plastic syringe fitted with a 27 gauge, ½ inch needle. Immediately following Evan's Blue injection, the guinea pig is injected intracutaneously at each of 2 sites in the shaved dorsal midline with 0.1 ml of the prepared argon-saturated LTB₄ solution (1 μg/1.0 ml). A third site is intracutaneously injected with the argon-saturated 0.25% bovine albumin in phosphate-buffered saline to serve as a vehicle control.

2 hours after challenge, the guinea pigs are euthanized by inhalation of carbon dioxide. Carbon dioxide is administered by inserting a rubber tube from the tank into a plastic bag containing the caged group of guinea pigs. Asphyxiation occurs in approximately 5 minutes.

After death, the dorsal skins are reflected to enable the measurement of 2 perpendicular diameters of the resultant wheals. The area of each wheal is determined using the formula: Area=$\pi r^2$.

Calculations and Statistics

For each guinea pig, the mean of the wheal areas obtained for the 2 injections sites is established after correction is made for the effect of the wheal area induced by the 0.25% Bovine Albumin in Phosphate-Buffered Saline vehicle. Then, a mean area for each treatment group with its corresponding standard error is calculated.

The following equation is used to calculate the percent inhibition of vehicle treated control wheal area by treatment with test compound:

$$\frac{\text{Mean Wheal Area}_{[Control]} - \text{Mean Wheal Area}_{[Treated]}}{\text{Mean Wheal Area}_{[Control]}}$$

In multiple dose experiments, the dose of a test compound that will cause 50% inhibition ($ED_{50}$) can be calculated from the regression equation for the response as percent inhibition (y) and log dose (x) and estimating the ($ED_{50}$) from: $\hat{y}(50)=bx+m$ where:

$\hat{y}=50\%$ inhibition,
x=dose of test compound,
b=slope of dose response line and
m=intercept of the dose response line.

95% confidence limits of $ED_{50}$ are calculated from the regression equation by the method of Litchfield and Wilcoxon where:

$$ED_{25} = \hat{y}(25) = bx + m,$$
$$ED_{75} = \hat{y}(75) = bx + m \text{ and}$$

$$S = \frac{(ED_{75}/ED_{50}) + (ED_{50}/ED_{25})}{2}$$

where S is the slope function used to compute the limit factor $fED_{50}$ 2.77/$\sqrt{N}$ as $fED_{50}$=S. 2.77 is an estimator, N is the square root of the number of animals used for all the doses and $fED_{50}$ is the factor to determine the upper (RU) and lower (RL) limits of the $ED_{50}$ as: RU=$ED_{50} \times fED_{50}$ and RL=$ED_{50} \div fED_{50}$. Statistical significance of any inhibition caused by treatment with a test compound can be calculated by applying Student's t (two-tailed) to the data.

Validation and Specificity Studies

The 1 μg/0.1 ml/site challenge dose of LTB₄ was selected for the reproducibility, sensitivity and ease of measurement of the resultant wheal. Studies have indicated that size of wheals induced by LTB₄ is directly related to the dose administered.

2 hours of incubation after intradermal challenge with LTB₄ was selected as the routine timing for the study. Duration studies conducted evidenced the production of measurable, reproducible wheals at the 2 hour endpoint.

In view of the results obtained when compounds of the present invention are subjected to this test, it can be demonstrated that valuable properties as LTB₄ antagonists are indicated.

A further test which may be used to determine the ability of compounds of this invention to exhibit LTB₄ antagonist activities is as follows:

Guinea Pig Polymorphonuclear Leukocyte Aggregation Assay

Isolation of Guinea Pig PMNs 6 ml of 6% Na-caseinate (in saline) is injected intraperitoneally into 2 male guinea pigs (250–300 g) lightly anesthetized with $CO_2$ or ether. The following day (18–24 hours post injection) the animals are sacrificed by decapitation or $CO_2$ overdose according to the SOP for nonclinical laboratory study methods.

A midline section of abdominal skin is removed and 13 ml Hanks buffer (containing 500 μl 10 mM EDTA/500 ml Hanks) plus 2 ml 7% Na-citrate is injected into the peritoneal cavity. The guinea pig is rocked back and forth 5 times. A small incision is made on the left side of the midline of the abdominal wall (avoid cutting obvious blood vessels). Use a fire-polished pasteur pipette to transfer the buffer plus cells from the abdominal cavity to 2 washed Nalgene (Oak Ridge) centrifuge tubes (half of buffer and cells in each tube). The tubes are then filled to 50 ml with additional citrate-Hanks buffer and centrifuged at 4000 rpm for 10 minutes.

Each pellet is resuspended in 1 ml of citrate-Hanks and then diluted to 50 ml with the same buffer. The cells are incubated for 30 minutes at room temperature on a Hema-Tek aliquot mixer. The cells are filtered through 2 layers of gauze into 50 ml with plastic beakers to remove PMN aggregates and then transferred to fresh, washed, 50 ml Nalgene centrifuge tubes.

The cells are centrifuged for 5 minutes, resuspended in 50 ml of fresh buffer, centrifuged again and then resuspended in 3 ml of citrate-free Hanks buffer. (Following any centrifugation the cells are always resuspended first in 1 ml of the desired fresh buffer.)

An aliquot of the washed cells, diluted 50-fold, is counted using a microscope and a hemacytometer.

The PMNs are counted as follows:

1. Dilute 50 $\mu$l of cells into 450 $\mu$l of Hank's buffer.
2. Dilute 50 $\mu$l of (1) with 150 $\mu$l of Hank's buffer plus 50 $\mu$l of Toluidine blue (50 x total dilution). Add 10 $\mu$l of (2) to the hemacytometer and count cells in 16 large squares (volume counted = 1 $\mu$l). View the hemacytometer under 40 x magnification. The unstained cells are PMNs.

Calculation: assume 149 cells are counted.

$$\frac{\text{\# of cells counted/ml} \times \text{dilution factor} \times 2 \text{ ml}}{\text{desired final cell concentration}} =$$

Final volume of buffer needed/ml of cells cells/ml = 149/.0001 = 1,490,000 cells/ml $$\frac{1.49 \times 10^6 \times 50 \times 1}{3 \times 10^7} = \frac{7.45 \times 10^8}{3 \times 10^7} =$$

2.48 ml/ml of cells counted

Thus, cells must be diluted 2.48-fold with Hanks buffer (2.48×3=7.44 ml; 7.44−3.0=4.44; add 4.44 ml buffer to the 3 ml of washed cells). This results in 7.44 ml of cells at a concentration of 3×10$^7$ cells per ml.

Instrument Adjustments

Place cuvettes containing 1×10$^7$ cells/ml (166 $\mu$l PMNs plus 334 $\mu$l buffer) plus flea magnets in the aggregometer sample wells. Turn on the *Chart Advance* to 30 cm/hr. Turn the attenuation dials to mid range and decrease the recorder mV range settings to 50 mV full scale. Press the red "zero" button on the aggregometer and note exactly the position of the recorder pens. Turn the aggregometer left hand "PPP" dials for each cuvette position to the left or right so that the associated recorder pens move to the exact positions noted by pressing the red "zero" button. The electrical circuits are now "balanced". Except for small balance adjustments, do not make any further changes in pen positions by adjusting the "PPP" dials.

Withdraw one of the cuvettes from the aggregometer and note the (positive) direction of recorder pen motion. Replace the cuvette. Using the recorder zero knob, move the recorder pen in the positive direction to the chart paper 95% line. The pens now should not move when the red "zero" button is pressed. The pen also should not move when the mV sensitivity range is changed to 20 or 10 mV full scale (leave at 10 mV).

PMN aggregation should cause the pen to move in the "negative" direction across the chart paper. Make comparable adjustments for the second aggregometer channel but zero the recorder pen on the opposite side of the chart paper. Finally, pressing the zero button on either the recorder or the aggregometer should not cause the pens to move more than a mm or two. This instrument configuration will result in maximal pen deflection following aggregation of cells.

Aggregation Studies

To a cuvette containing 334 $\mu$l of buffer and a flea magnet, add 166 $\mu$l of PMNs, 10 $\mu$l of Ca$^{++}$/Mg$^{++}$ (70/et mM; 1.4/0.7 mM final) and 5 $\mu$l of 10 $\mu$M cytochalasin-$\beta$ allow to warm up in the aggregometer (37° C.) for 5 minutes and then add 1 $\mu$l of test compound in DMSO or DMSO carrier alone. Note compound effects, if any, for 2 minutes, then add 5$\mu$l of the challenge agonist (LTB$_4$, PAF, etc.) and observe the response for at least 2 minutes. The standard concentrations of agonists used in this assay are arachidonic acid, 6 $\mu$M; LTB$_4$, 0.3 nM; PAF, 30 pM; and FMLP, 0.6 nM.

Aggregation is quantitated by measuring, in millimeters, the average maximum deflection of the pen line at 1 minute or less after the addition of LTB$_4$. The maximum response to a control challenge with arachidonic acid may develop somewhat more slowly than this.

Each aggregometer-recorder channel should include its own series of control aggregations. All compounds should be tested at least twice at each concentration of interest. The inhibitory activity observed is expressed as the mean percent change (inhibition) observed relative to the controls determined in that channel. Controls must include appropriate solvent blanks.

The results of the above test demonstrate that compounds within the scope of this invention inhibit the activity of LTB$_4$.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, trochees, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained.

Preferred compositions or preparations according to the present invention are prepared so that an oral dosage unit form contains between about 50 and 300 mg of active compound.

The tablets, trochees, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxy-propylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100 M/day or from about 0.1 mg to about 50 mg/kg of body weight per day and higher although it may be administered in several different dosage units. Higher dosages are required for oral administration.

The compounds of the present invention may be prepared by the following representative examples:

EXAMPLE 1

3-Cinnamyloxy-5-[(N-methyl-N-phenethyl)carbamoylmethyl)phenyl acetic acid

Step A: Methyl,methyl 5-hydroxyisophthalate

To a solution of 30 g (0.165 moles) of 5-hydroxyisophthalic acid in 500 ml MeOH is bubbled in dry HCl gas for 20 minutes. The reaction mixture is then allowed to stir at room temperature for 2 hours and it is then concentrated down in vacuo to yield methyl,-methyl 5-hydroxyisophthalate which is used directly in the next step.

Step B: Methyl,methyl 5-methoxyisophthalate

To a solution of 34.6 g (0.165 moles) of methyl,methyl 5-hydroxyisophthalate in 500 ml acetone is added 28.43 g (0.206 moles) of $K_2CO_3$ and 12.84 ml (0.206 moles) of MeI. The reaction mixture is refluxed for 5 hours, filtered and concentrated down in vacuo. The resulting crude solid is dissolved in EtOAc, washed with $H_2O$ (2 times), brine, dried with $MgSO_4$, filtered and concentrated in vacuo to yield methyl,methyl 5-methoxyisophthalate which is used directly in the next step.

Step C: 1,3-di-(hydroxymethyl)-5-methoxybenzene

To a solution of 5.00 g (22.32 mmoles) of methyl,-methyl 5-methoxyisophthalate in 100 ml dry THF is added dropwise, maintaining a gentle reflux, 67 ml (66.96 mmoles) of a 1M solution of lithium aluminum hydride in $Et_2O$. After addition the reaction mixture is stirred for 1 hour and is then quenched with saturated $NH_4Cl$. The reaction mixture is then extracted with $Et_2O$ (3 times). The $Et_2O$ layers are combined, washed with brine, dried with $MgSO_4$, filtered and concentrated down in vacuo to yield 1,3-di-(hydroxymethyl)-5-methoxybenzene which is used directly in the next step.

Step D: 1,3-di-(bromomethyl)-5-methoxybenzene

A suspension of 9.25 g (55.06 mmoles) of 1,3-di-(hydroxymethyl)-5-methoxybenzene in 75 ml of benzene is added dropwide to 9.4 ml (99.11 mmoles) $PBr_3$ as a solution in 15 ml benzene. After addition, the reaction mixture is refluxed for 45 minutes, filtered and poured onto 100 g of ice. The reaction mixture is then extracted with EtOAc (3 times). The EtOAc layers are combined and are dried with $MgSO_4$, filtered and concentrated in vacuo to afford 1,3-di-(bromomethyl)-5-methoxybenzene which is used directly in the next step.

Step E: 1,3-di-(cyanomethyl)-5-methoxybenzene

To a solution of 23.35 g (79.42 mmoles) of 1,3-di-(bromomethyl)-5-methoxybenzene in 300 ml toluene is added 300 ml of $H_2O$, 11.67 g (238.26 mmoles) of NaCN and 0.58 g Adogen ® 464*. The reaction mixture is then refluxed for 18 hours and then allowed to come to room temperature. The organic layer is separated and washed with $H_2O$ (3 times), brine (2 times), dried with $MgSO_4$ and filtered. To this is added 10 mls of EtOH and the resulting reaction mixture is filtered through silica gel and is concentrated in vacuo to yield 1,3-di-(cyanomethyl)-5-methoxybenzene which is used directly in the next step. [*Adogen ®464 (methyltriallyl ($C_8$-$C_{10}$) ammonium chloride) Aldrich 50934-77-5]

Step F: 3,5-di-(carbmethoxymethyl)phenol

To a solution of 9.67 g (52 mmoles) of 1,3-di-(cyanomethyl)-5-methoxybenzene in 90 ml acetic acid is added 90 mls of a 48% HBr solution. The reaction mixture is refluxed for 18 hours, poured into $H_2O$ and extracted with EtoAc. The EtoAc extractions are combined, washed with $H_2O$ (3 times), brine (1 time), dried with $MgSO_4$, filtered and concentrated in vacuo. The resulting product is taken up in 100 ml of MeOH and dry HCl gas is bubbled in for 10 minutes. The reaction mixture is stirred for 30 minutes at room temperature and concentrated in vacuo. Purification by flash chromatography gives 3,5-di-(carbmethoxymethyl)phenol which is used directly in the next step.

Step G: 1,3-di-(carbomethoxymethyl)-5-cinnamyloxybenzene

To a solution of 2.00 g (9.0 mmoles) if 3,5-di-(carbmethoxymethyl)phenol in 75 ml acetone is added 1.24 g (9.0 mmoles) of $K_2CO_3$ followed by 1.77 g (9.0 mmoles) of cinnamylbromide. This reaction mixture is refluxed for 2 hours, cooled to room temperature, filtered and concentrated down in vacuo. Purification by flash chromatography affords 1,3-di-(carbomethoxymethyl)-5-cinnamyloxybenzene which is used directly in the next step.

Step H: 1,3-di-(carboxymethyl)-5-cinnamyloxybenzene

To a solution of 2.98 g (8.82 mmoles) of 1,3-di-(carbomethoxymethyl)-5-cinnamyloxybenzene in 50 ml EtOH is added 26 ml of 1N NaOH. After 12 hours, the reaction mixture is concentrated down in vacuo, taken up in $H_2O$ and acidified to pH 4 with 1N HCl. The solid precipitate is collected and recrystallized from MeOH to afford 1,3-di-(carboxymethyl)-5-cinnamyloxybenzene which is used directly in the next step.

Step I: Methyl 3-cinnamyloxy-5-[(N-methyl-N-phenethyl)carbamoylmethylphenylacetate To a suspension of 2.53 g (8.16 mmoles) of 1,3-di-(carboxymethyl)-5-cinnamyloxybenzene in 75 ml $CH_2Cl_2$ is added 2.64 g (16.32 mmoles) of 1,1'-carbonyldiimadazole. After 20 minutes 1.19 ml (8.16 mmoles) of N-methyl-N-phenethylamine is added dropwise. After stirring for 4 hours, 261 mg (8.16 mmoles) of MeOH and 20 mg of 4-dimethylaminopyridine is added. The reaction mixture is stirred for 12 hours after which time it is concentrated down in vacuo. Purification by flash chromatography gives methyl 3-cinnamyloxy-5-[(N-methyl-N-phenethyl)carbamoylmethyl]phenylacetate. NMR confirms this structure which is used directly in the next step.

Step J: 3-cinnamyloxy-5-(N-methyl-N-phenethyl)carbamoylmethyl]phenylacetic acid A solution of 1.73 g (3.92 mmoles) of methyl 3-cinnamyloxy-5-[(N-methyl-N-phenethyl)carbamoylmethyl]phenylacetate in 25 ml EtOH is added 8 ml of 1N NaOH. After 12 hours, the reaction mixture is concentrated down in vacuo, taken up in $H_2O$ and acidified to pH 3 with 1N HCl. The resulting precipitate is collected to give 3-cinnamyloxy-5-[(N-methyl-N-phenethyl)carbamoylmethyl]phenylacetic acid. (m.p. 129°–132° C.)

EXAMPLE 2

When the procedure of Example 1 is followed and benzyl bromide or phenethyl bromide are used in place of cinnamylbromide in Step G, then the products prepared are 1,3-di-(carbomethoxymethyl)-5-benzyloxybenzene and 1,3-di-(carbomethoxymethyl)-5-phenethyloxybenzene. These compounds are hydrolyzed in the same manner as Example 1, Step H to obtain 1,3-di-(carboxymethyl)-5-benzyloxybenzene and 1,3-di-(carboxymethyl)-5-phenethyloxybenzene.

EXAMPLE 3

When 3,5-di-(carboxymethyl)-5-cinnamyloxybenzene of Example 1, Step I is replaced by 1,3-di-(carboxymethyl)-5-benzyloxybenzene and 1,3-di-(carboxymethyl)-5-phenethyloxybenzene then the products prepared through Step J are 3-benzyloxy-5-[(N-methyl-N-phenethyl)carbamoylmethyl]phenylacetic acid (m.p. 49°–52° C.) and 3-phenethyloxy-5-[(N-methyl-N-phenethyl)carbamoylmethyl]phenylacetic acid. NMR confirms these structures.

EXAMPLE 4

When the procedure of Examples 1 and 3 are followed and N-methyl-N-phenethylamine of Step I is replaced with N-ethyl-N-phenethylamine, N-methyl-N-phenprop-2-ylamine, N-methyl-N-benzylamine, N-methyl-N-phenpropylamine or N-phenethylamine then the corresponding products are obtained.

EXAMPLE 5

When 3,5-di-(carbomethoxymethyl)phenol of Example 1, Step G is replaced by 3,5-di-(carbomethoxymethoxy)phenol then the products prepared through Step J are 1,3-di(carbomethoxymethoxy)-5-cinnamyloxybenzene, 1,3-di(carboxymethoxy)-5-cinnamyloxybenzene, methyl 3-cinnamyloxy-5-[(N-methyl-N-phenethyl)carbamoylmethoxy]phenoxyacetate and 3-cinnamyloxy-5-

[(N-methyl-N-phenethyl)carbamoylmethoxy]phenoxyacetic acid. These compounds are confirmed by NMR.

EXAMPLE 6

Methyl 3-cinnamyloxy-5-(N-methyl-N-phenethyl)carbamoylmethyl]phenoxyacetate

3-Cinnamyloxy-5-(N-methyl-N-phenethyl)carbamoylmethyl]phenoxyacetic acid

Step A: When 3,5-di-(carbomethoxymethyl)phenol of Example 1, Step G is replaced by methyl 3-hydroxy-5-carbomethoxymethoxyphenylacetate, then the product prepared is methyl 3-cinnamyloxy-5-carbomethoxymethoxyphenylacetate.

Step B: When the product of Step A is hydrolyzed according to the procedure of Example 1, Step H then the product prepared is 3-cinnamyloxy-5-carboxymethoxyphenylacetic acid.

Step C: Treatment of the product of Step B according to the procedure of Example 1, Step I affords methyl 3-cinnamyloxy-5-[(N-methyl-N-phenethyl)carbamoylmethyl]phenoxyacetate. NMR confirms this structure.

Step D: Hydrolysis of the product from Step C according to the procedure of Example 1, Step J gives 3-cinnamyloxy-5-[(N-methyl-N-phenethyl)carbamoylmethyl]phenoxyacetic acid. NMR confirms this structure.

EXAMPLE 7

When the procedure of Example 6 is followed and cinnamylbromide is replaced by benzylbromide in Step A, then the products prepared from Step C and D are methyl 3-benzyloxy-5-[(N-methyl-N-phenethyl)carbamoylmethyl]phenoxyacetate (NMR) and 3-benzyloxy-5-[(N-methyl-N-phenethyl)carbamoylmethyl]-phenoxyacetic acid. (m.p. 112°-115° C.)

EXAMPLE 8

2-[(N-methyl-N-phenethyl)carbamoylmethoxy]-4-benzyloxy-1-carboxyvinylbenzene

Step A: 4-benzyloxy-2-hydroxybenzaldehyde

A mixture of 2,4-dihydroxybenzaldehyde (5.52 g, 0.04 mmol), benzylbromide (5.7 ml, 0.048 mmol) and $K_2CO_4$ (6.64 g) in 90 ml of 2-butanone is stirred for 48 hours at room temperature and then heated to reflux for 8 hours. After cooling to room temperature and filtering, the filtrate is concentrated in vacuo and the residue chromatographed (25% EtOAc/Hexane) to obtain 4-benzyloxy-2-hydroxybenzaldehyde which is used directly in the next step.

Step B: 2-carbomethoxyvinyl-5-benzyloxyphenol

A solution of 4-benzyloxy-2-hydroxybenzaldehyde (1.14 g, 5 mmol) and methyl(triphenylphosphoranylidene)acetate (3.51 g, 10 mmol) in THF (40 ml) is stirred at room temperature for 18 hours. The reaction mixture is then concentrated in vacuo and the residue purified by dry column chromatography using 25% EtOAc in hexane to 2:1/hexane:EtOAc. The concentrated residue is triturated with EtOAc/ether to obtain 2-carbomethoxyvinyl-5-butoxyphenol which is confirmed by NMR and used directly in the next step.

Step C: 2-[(N-methyl-N-phenethyl)carbamoylmethoxy]-4-benzyloxy-1-carbomethoxyvinylbenzene A mixture of 2-carbomethoxyvinyl-5-benzyloxyphenol (0.283 g, 1 mmol), N-methyl-N-phenethylcarbamylmethylbromide (0.38 g, 1.5 mmol) and $K_2CO_3$ (207 mg, 1.5 mmol) in 10 ml 2-butanone is heated at 80° C. for 18 hours. The reaction mixture is concentrated and ethyl acetate (25 ml) added. The mixture is washed weith brine, dried and concentrated in vacuo to obtain 2-[(N-methyl-N-phenethyl)carbamoylmethoxy]-4-benzyloxy-1-carbomethoxyvinylbenzene.

Step D: 2-[(N-methyl-N-phenethyl)carbamoylmethoxy]-4-benzyloxy-1-carboxyvinylbenzene Following the procedure of Example 1, Step J the ester of Step C above is hydrolyzed and recrystallized from EtOAc/ether to give 2-[(N-methyl-N-phenethyl)-carbamoylmethoxy]-4-benzyloxy-1-carboxyvinyl-benzene. (m.p. 114°-116° C.) NMR confirms this structure.

EXAMPLE 9

3-[(N-methyl-N-phenethyl)carbamoylmethyl]-5-(N-methyl-N-phenethyl)carbamoylmethoxy]-1-carboxymethoxybenzene Step A: Ethyl 3,5-dihydroxyphenylacetate To a solution of ethyl 3,5-dimethoxyphenylacetate (11.0 g, 52,32 mmol) in 200 ml of $CH_2Cl_2$ is added 75 ml (25 mmol, 1.4 eq) of 1.0M $BBr_3$ in $CH_2Cl_2$. This is then refluxed for 36 hours. The mixture is concentrated in vacuo, then partitioned between EtOAc and HCl. The organics are dried ($MgSO_4$) and concentrated in vacuo. This is then redissolved in EtOH and HCl is bubbled in for 5 minutes and then stirred overnight at room temperature. The mixture is concentrated in vacuo, then partitioned between EtOAc and saturated $NaHCO_3$ solution. The organics are dried ($MgSO_4$) and concentrated in vacuo. This is then chromatographed using silica gel and eluted with $Et_2O$. The filtrate is concentrated in vacuo to obtain ethyl 3,5-dihydroxyphenylacetate which is confirmed by NMR and used directly in the next step.

Step B: Ethyl 3,5-dibenzyloxyphenylacetate

A solution of ethyl 3,5-dihydroxyphenylacetate (4.0 g, 20.39 mmol), benzyl bromide (4.85 ml, 6.97 g, 40.77 mmol, 2 eq) and 5.64 g (40.77 mmol, 2 eq) of $K_2CO_3$ in 100 ml of acetone is refluxed overnight. The mixture is concentrated in vacuo, then partitioned between EtOAc and $H_2O$. The organics are dried ($MgSO_4$) and concentrated in vacuo. This is then passed through a flash silica gel column that is slurry packed with hexanes and eluted with 10% EtOAc in hexanes. Concentration of desired fractions gives ethyl 3,5-dibenzyloxyphenylacetate which is confirmed by NMR and used directly in the next step.

Step C: 3,5-dibenzyloxyphenylacetic acid

To a solution of ethyl 3,5-dibenzyloxyphenylacetate (4.1 g, 10.9 mmol) in 50 ml of EtOH is added 21 ml (6 eq) of 1N NaOH. The reaction is stirred at room temperature for 2 hours at which time it is extracted with $Et_2O$ and $H_2O$. The $H_2O$ layer is acidified to pH~1 using 1N HCl and extracted with $Et_2O$. The organics are dried ($MgSO_4$) and concentrated in vacuo to obtain 3,5-dibenzyloxyphenylacetic acid which is confirmed by NMR and used directly in the next step.

Step D:
3,5-dibenzyloxy-1-(N-methyl-N-phenethyl)carbamoylmethyl]benzene

To a solution of 3,5-dibenzyloxyphenylacetic acid (3.53 g, 10.10 mmol) in 50 ml of $CH_2Cl_2$ is added 1.80 g (11.11 mmol, 1.1 eq) 1,1′-carbonyldiimidazole. This is stirred at room temperature for 1½ hours at which time 1.62 ml (1.50 g, 11.11 mmol, 1.1 eq) of N-methyl-N-phenethyl amine is added. This is stirred at room temperature for 2 hours, concentrated in vacuo, then partitioned between EtOAc and 1N HCl. The organics are washed with saturated $NaHCO_3$, dried ($MgSO_4$) and concentrated in vacuo to give 3,5-dibenzyloxy-1-[(N-methyl-N-phenethyl)carbamoylmethyl]benzene as a yellow oil which is confirmed by NMR and used directly in the next step.

Step E:
3-benzyloxy-5-(N-methyl-N-phenethyl)carbamoylmethyl]phenol

To a solution of 3,5-dibenzyloxy-1-[(N-methyl-N-phenethyl)carbamoylmethyl]benzene (2.7 g, 5.80 mmol) in 50 ml of $CH_2Cl_2$ is added 1.93 ml (1.93 mmol, 1. eq) of 1.0M $BBr_3$ in $CH_2Cl_2$. This is then stirred at room temperature overnight. The mixture is concentrated in vacuo, then partitioned between EtOAc and 1N HCl. The organics are dried ($MgSO_4$) and concentrated in vacuo. This is passed through a flash silica gel column that is slurry packed with hexanes and eluted with 30% EtOAc in hexanes. Concentration of desired fractions in vacuo gives 3-benzyloxy-5-[(N-methyl-N-phenethyl)-carbamoylmethyl]phenol as a clear oil which is confirmed by NMR and used directly in the next step.

Step F:
N-methyl-N-phenethylcarbamoylmethylbromide

A solution of 14.19 ml (27.07 g, 171.95 mmol) of bromoacetyl chloride in 100 ml of $CH_2Cl_2$ at $-25°$ C. is dropped in 50 ml (46.5 g, 343.91 mmol, 2 eq) of N-methyl-N-phenethylamine in 50 ml of $CH_2Cl_2$ over a period of 1½ hours. This is then stirred at $-25°$ C. for 15 minutes, allowed to equilibrate to room temperature where it is stirred for ½ an hour and then partitioned between $CH_2Cl_2$, $H_2O$ and 2N HCl. The organics are dried ($MgSO_4$) and concentrated in vacuo to give N-methyl-N-phenethylcarbamoylmethylbromide as a yellow oil. This is confirmed by NMR and used directly as follows.

3-benzyloxy-5-[(N-methyl-N-phenethyl)carbamoylmethoxy]-1-[(N-methyl-N-phenethyl)carbamoylmethyl]-benzene A solution of 3-benzyloxy-5-[(N-methyl-N-phenethyl)carbamoylmethyl]phenol 0.666 g, (1.77 mmol), 0.43 g (1.77 mmol) of N-methyl-N-phenethylcarbamoylmethylbromide and 0.25 g (1.77 mmol) of $K_2CO_3$ in 75 ml of acetone are refluxed for 4 hours, then concentrated in vacuo. This residue is partitioned between EtOAc and $H_2O$. The organics are dried ($MgSO_4$) and concentrated in vacuo, then passed through a flash silica gel column that is slurry packed with hexanes and eluted with 60% EtOAc in hexanes. Concentration of desired fractions gives 3-benzyloxy-5-[(N-methyl-N-phenethyl)carbamoylmethoxy]-1-[(N-methyl-N-phenethyl) carbamoylmethyl]benzene as a clear oil which is confirmed by NMR and used directly in the next step.

Step G:
3-(N-methyl-N-phenethyl)carbamoylmethyl]-5-[(N-methyl-N-phenethyl)carbamoylmethoxy]phenol To a solution of 3-benzyloxy-5-[(N-methyl-N-phenethyl)carbamoylmethoxy]-1-[(N-methyl-phenethyl)carbamoylmethyl]benzene (0.77 g, 1.40 mmol) in 30 ml of $CH_2Cl_2$ is added 1.4 ml (1.40 mmol, 1 eq) of 1.0M $BBr_3$ in $CH_2Cl_2$. This is then stirred at room temperature overnight. The mixture is concentrated in vacuo, then partitioned between 1N HCl and EtOAc. The organics are dried ($MgSO_4$) and concentrated in vacuo. This is passed through a flash silica gel column that is slurry packed with hexanes and eluted with 50% EtOAc in hexanes. Concentration of desired fractions gives 3-[(N-methyl-N-phenethyl)carbamoylmethyl]-5-[(N-methyl-N-phenethyl) carbamoylmethoxy]phenol which is confirmed by NMR and used directly in the next step.

Step H:
3-(N-methyl-N-phenethyl)carbamoylmethyl]-5-(N-methyl-N-phenethyl)carbamoylmethoxy]-1-((carbo-t-butoxy) methoxy)benzene A solution of 3-[(N-methyl-N-phenethyl)carbamoylmethyl]-5-[(N-methyl-N-phenethyl)-carbamoylmethoxy]phenol 0.3 g (0.65 mmol), 0.11 ml (1.27 g, 0.65 mmol) of t-butyl bromoacetate and 0.18 g (1.3 mmol, 2 eq) of $K_2CO_3$ in 50 ml of acetone is refluxed overnight. The mixture is concentrated in vacuo, then partitioned between EtOAc and $H_2O$. The organics are dried ($MgSO_4$) and concentrated in vacuo. This is then passed through a flash silica gel column slurry packed with hexanes and eluted with 40% acetone in hexanes. Concentration of desired fractions gives 3-[(N-methyl-N-phenethyl)carbamoylmethyl]-5-[(N-methyl-N-phenethyl)carbamoylmethoxy]-1-((carbo-t-butoxy) methoxy)benzene as a clear oil which is confirmed by NMR and used directly in the next step.

Step I:
3-[(N-methyl-N-phenethyl)carbamoylmethyl]-5-(N-methyl-N-phenethyl)carbamoylmethoxy]-1-carboxymethoxybenzene A solution of 3-[(N-methyl-N-phenethyl)carbamoylmethyl]-5-[(N-methyl-N-phenethyl) carbamoylmethoxy]-1-((carbo-t-butoxy)methoxy)benzene 0.3 g (0.52 mmol) in 30 ml of 2/1 $CH_2Cl_2/CF_3CO_2H$ is stirred overnight at room temperature. The mixture is concentrated in vacuo, then partitioned between EtOAc and $H_2O$. The organics are dried ($MgSO_4$) and concentrated in vacuo. This is applied to a prep thick layer plate and developed in 10% MeOH in $CH_2Cl_2$. Removal of desired band and elution with 10% MeOH in $CH_2Cl_2$ gives 0.16 g of 3-[(N-methyl-N-phenethyl)carbamoylmethyl]-5-[(N-methyl-N-phenethyl)carbamoylmethoxy]-1-carboxymethoxybenzene. This is confirmed by NMR and mass spec.

Calc'd: C, 69.48; H, 6.61; N, 5.40;
Found: C, 69.85; H, 6.68; N, 5.39.

EXAMPLE 10

3-[(N-methyl-N-phenethyl)carbamoylmethyl]-5-benzyloxy-1-(3-carboxy-2-propenyloxy)benzene

Step A:
3-[(N-methyl-N-phenethyl)carbamoylmethyl]-5-benzyloxyphenol

To a solution of 6.7 g (14.39 mmol) of 3,5-dibenzyloxy-1-[(N-methyl-N-phenethyl)carbamoylmethyl]-benzene in 50 ml of $CH_2Cl_2$ is added 4.80 ml (4.80 mmol, 0.33 eq) of 1.0M $BBr_3$ in $CH_2Cl_2$. This is allowed to stir over the weekend at room temperature then concentrated in vacuo and partitioned between EtOAc and 1N HCl. The organics are dried ($MgSO_4$) and concentrated in vacuo. This is passed through a flash silica gel column that is slurry packed with hexanes and eluted with 30% EtOAc in hexanes. Concentration of desired fractions gives 3-[(N-methyl-N-phenethyl)carbamoylmethyl]-5-benzyloxyphenol which is confirmed by NMR and used directly in the next step.

Step B:
3-[(N-methyl-N-phenethyl)carbamoylmethyl]-5-benzyloxy-1-carbomethoxyvinyloxybenzene To a solution of 1.5 g (3.99 mmol) of 3-[(N-methyl-N-phenethyl)carbamoylmethyl]-5-benzyloxyphenol, 0.57 ml (0.874 g, 4.88 mmol, 1.1 eq of 90%) of methyl 4-bromocrotonate and 0.61 g (4.39 mmol, 1.1 eq) of $K_2CO_2$ and refluxed overnight in 100 ml of acetone. The mixture is concentrated in vacuo, then partitioned between EtOAc and $H_2O$. The organics are dried ($MgSO_4$) and concentrated in vacuo then passed through a flash silica gel column that is slurry packed with hexanes and eluted with 40% EtOAc in hexanes. Desired fractions are concentrated in vacuo to give 3-[(N-methyl-N-phenethyl)carbamoylmethyl]-5-benzyloxy-1-(3-carbomethoxy-2-propenyloxy)benzene which is confirmed by NMR and used directly in the next step.

Step C:
3-(N-methyl-N-phenethyl)carbamoylmethyl]-5-benzyloxy-1-(3-carboxy-2-propenyloxy)benzene A solution of 0.48 g (1.01 mmol) of 3-[(N-methyl-N-phenethyl)carbamoylmethyl]-5-benzyloxy-1-(3-carbomethoxy-2-propenyloxy)benzene and 20 ml (2.00 mmol, 2 eq) of 1N NaOH in 30 ml of MeOH is stirred for 3 hours at room temperature. This is acidified to pH~1 using 1N HCl and partitioned between EtOAc and $H_2O$. The organics are dried ($MgSO_4$) and concentrated in vacuo. The mixture is basified with 1N NaOH, then partitioned between $Et_2O$ and $H_2O$. This is extracted 3 times with $Et_2O$. The $H_2O$ is acidified to pH~1 using 1N HCl, then extracted with EtOAc. The organics are dried and concentrated in vacuo. The mixture is chromatographed using silica gel and developed in 10% MeOH in $CH_2Cl_2$. The filtrate is dried in vacuo to obtain 3-[(N-methyl-N-phenethyl)carbamoylmethyl]-5-benzyloxy-1-(3-carboxy-2-propenyloxy)benzene. This is confirmed by NMR and mass spec.

Calc'd: C, 73.18; H, 6.36; N, 3.05;
Found: C, 72.57; H, 6.50; N, 2.94.

EXAMPLE 11

When the procedure of Example 10 is followed and methyl 4-bromocrotonate in Step B is replaced by methyl 4-bromopentanoate, methyl 5-bromopentanoate, methyl 3-bromopropanoate or methyl 2-bromobutanoate then the corresponding products are prepared.

EXAMPLE 12 trans-N-methyl-N-phenethyl-2-[4-benzyloxy-3-(2-carboxyvinyl)phenyl]acetamide

Step A: 6-bromomethylcoumarin

To a solution of 500 g (31.25 mmoles) of 6-methylcoumarin in 200 ml $CCl_4$ is added 5.56 g (31.25 mmoles) of NBS. This solution is subjected to a sunlamp at reflux for 4¼ hours. After cooling, the reaction mixture is filtered and the filtrate concentrated in vacuo to yield a solid which upon trituration with ethyl acetate affords 6-bromomethylcoumarin which is used directly in the next step.

Step B: 6-cyanomethylcoumarin

To a solution of 8.43 g (35.27 mmoles) of 6-bromomethylcoumarin in 60 ml DMSO is added 1.73 g (35.27 mmoles) of NACN slowly. After 2 hours the reaction mixture is poured into $H_2O$ and is extracted with EtOAc (3 times). The EtOAc layers are combined, washed with brine (1 time), dried with $MgSO_4$, filtered and concentrated in vacuo. The crude product is purified by flash chromatography to yield 6-cyanomethylcoumarin which is used directly in the next step.

Step C: 6-carbomethoxymethylcoumarin

To a 0° C. solution of 2.58 g (13.95 mmoles) of 6-cyanomethylcoumarin in 100 ml MeOH is bubbled in dry HCl for 10 minutes. The reaction mixture is allowed to stir at room temperature for 12 hours after which time the reaction mixture is concentrated in vacuo. The product is taken up in ethylacetate and is washed with $H_2O$ (2 times), brine (1 time), dried with $MgSO_4$, filtered and concentrated in vacuo to yield 6-carbomethoxymethylcoumarin which is used directly in the next step.

Step D: cis-3-carboxyvinyl-4-benzyloxyphenylacetic acid

To a solution of 2.63 g (12.06 mmoles) of 6-carbomethoxymethylcoumarin in 50 ml of ethanol is added 2.41 g (60.30 mmoles) of NaOH in 3 ml of $H_2O$. The reaction mixture is heated to reflux for 8 hours after which time 40 ml (3.36 moles) of benzylbromide is added. The reaction mixture is stirred at room temperature for 12 hours after which time the reaction mixture is concentrated in vacuo. The crude product is taken up in $H_2O$, washed with ethylacetate (2 times) and acidified to pH 3–4 with concentrated HCl. The resulting white precipitate is collected to yield cis-3-carboxyvinyl-4-benzyloxyphenylacetic acid which is used directly in the next step.

Step E:
trans-N-methyl-N-phenethyl-2-[4-benzyloxy-3-(2carbomethoxyvinyl)phenyl]acetamide To a solution of 500 mg (1.61 mmoles) of cis-3-carboxyvinyl-4-benzyloxyphenylacetic acid in 30 ml of $CH_2Cl_2$ is added 522 mg (3.22 mmoles) of 1,1'-carbonyldiimidazole (CDI). After 30 minutes, 234 ml (1.61 mmoles) of N-methyl-N-phenethylamine is added. After 18 hours a catalytic amount of 4-dimethylaminopyridine and 5 ml of methanol are added. After stirring for 2½ hours, the reaction mixture is concentrated down in vacuo, taken up in ethyl acetate, washed with 1N NaOH, 1N HCl, H₂O (2 times), brine (2 times), dried with MgSO₄, filtered and concentrated in vacuo. The crude product is purified by flash chromatography to yield trans-N-methyl-N-phenethyl-2-[4-benzyloxy-3-(2-carbomethoxyvinyl)phenyl]acetamide. NMR confirms this structure which is used directly in the next step.

Step F:
trans-N-methyl-N-phenethyl-2-[4-benzyloxy-3-(2-carboxyvinyl)phenyl]acetamide To a solution of 160 mg (0.36 mmoles) of trans-N-methyl-N-phenethyl-2-[(4-benzyloxy-3-(2-carbomethoxyvinyl)phenyl]acetamide in 10 ml of a 1:1:1 MeOH/THF/H₂O mixture at 0° C. is added 76 mg (1.8 mmoles) of LiOH·H₂O. The reaction mixture is allowed to come to room temperature and stirred at room temperatured for 12 hours after which time the eraction mixtured is concentrated down in vacuo, taken up in H₂O washed with ether (2 times) and acidified to pH 3-4 with 1N HCl. The aqueous layer is extracted with ether (2 times). The ether extracts are combined and are dried with MgSO₄, filtered and concentrated down in vacuo to give trans-N-methyl-N-phenethyl-2-[4-benzyloxy-3-(2-carboxyvinyl)phenyl]acetamide. (m.p. 56°-58° C.)

EXAMPLE 13 cis-N-methyl-N-phenethyl-2-[4-benzyloxy-3-(2-carboxyvinyl)phenyl]acetamide

Step A: Methyl cis-3-carbomethoxyvinyl-4-benzyloxyphenyl acetate

To a solution of 1.82 g of cis-3-carboxyvinyl-4-benzyloxyphenylacetic acid in 70 ml methanol is bubbled in dry HCl gas for 5 minutes. After stirring at room temperature for 3 hours, the reaction mixture is concentrated in vacuo, taken up in EtOAc, washed with saturated sodium bicarbonate, H₂O, brine, dried with MgSO₄, filtered and concentrated in vacuo to yield methyl cis-3-carbomethoxyvinyl-4-benzyloxyphenyl acetate which is used directly in the next step.

Step B:
cis-3-carbomethoxyvinyl-4-benzyloxyphenylacetic acid

To a solution of 1.86 g (5.49 mmoles) of methyl cis-3-carbomethoxyvinyl-4-benzyloxyphenyl acetate in 50 ml of 1:1:1 solution of MeOH/THF/H₂O at 0° C. is added 230 mg (5.49 mmoles) LiOH·H₂O. After addition, the reaction mixture is allowed to come to room temperature and stirred for 18 hours. After this, the reaction is concentrated in vacuo, taken up in H₂O, washed with ether, acidified to pH 4 with 1N HCl and extracted with ethyl acetate (2 times). The ethyl acetate layers are combined, washed with brine, dried with MgSO₄, filtered and concentrated in vacuo to yield cis-3-carbomethoxyvinyl-4-benzyloxyphenylacetic acid which is used in the next step.

Step C:
cis-N-methyl-N-phenethyl-2-[4-benzyloxy-3-(2-carbomethoxyvinyl)phenyl]acetamide To a solution of 1.85 g (5.69 mmoles) of cis-3-carbomethoxyvinyl-4-benzyloxyphenylacetic acid in 50 ml of CH₂Cl₂ is added 1.02 g (6.26 mmoles) if 1,1'-carbonyldiimadazole. After 15 minutes, 827 ml (5.69 mmoles) of N-methyl-N-phenethylamine is added. After 5 hours, the reaction mixture is concentrated in vacuo and is purified flash chromatography to yield cis-N-methyl-N-phenethyl-2-[4-benzyloxy-3-(2-carbomethoxyvinyl)phenyl]acetamide which is used directly in the next step.

Step D:
cis-N-methyl-N-phenethyl-2-4-benzyloxy-3-(2-carboxyvinyl)phenyl]acetamide To a solution of 160 mg (0.36 mmoles) of cis-N-methyl-N-phenethyl-2-[4-benzyloxy-3-(2-carbomethoxyvinyl)phenyl]acetamide in 10 ml of a 1:1:1 MeOH/THF/H₂O mixture at 0° C. is added 76 mg (1.8 mmoles) of LiOH·H₂O. The reaction mixture is allowed to come to room temperature and stirred at room temperatured for 12 hours after which time the eraction mixtured is concentrated down in vacuo, taken up in H₂O washed with ether (2 times) and acidified to pH 3-4 with 1N HCl. The aqueous layer extracted with ether (2 times). The ether extracts are combined and are dried with MgSO₄, filtered and concentrated down in vacuo to give cis-N-methyl-N-phenethyl-2-[4-benzyloxy-3-(2-carboxyvinyl)phenyl]acetamide. (m.p. 48°-51° C.)

EXAMPLE 14

When the procedure of Examples 12 and 13 are followed and 6-methylcoumarin in Example 12, Step A is replaced by 8-chloro-6-methylcoumarin then the products prepared are trans-N-methyl-N-phenethyl-2-[4-benzyloxy-3-(2-carboxyvinyl)-5-chlorophenyl]acetamide and cis-N-methyl-N-phenethyl-2-[4-benzyloxy-3-(2-carboxyvinyl)-5-chlorophenyl]acetamide.

EXAMPLE 15

2-phenyl-5-[(N-methyl-N-phenethyl)carbamoylmethyl]carboxyvinylbenzene

Step A: Methyl 4-phenyl-3-carboethoxyvinylphenylacetate

To a suspension of NaOH (1.68 g, 80% dispersion in mineral oil, 56 mmol) in 150 ml of THF, stirred in an ice bath under an atmosphere of nitrogen, is added dropwise a solution of 11.25 ml (98% reagent, 54.45 mmol) of triethyl phosphonoacetate in 30 ml THF. The resulting mixture is stirred in an ice bath for an additional 20 minutes and a solution of 2-phenyl-5-carbomethoxymethylbenzaldehyde (7.88 g, 36.3 mmol) in 80 ml of THF is added quickly. The ice bath is then removed and the mixture stirred for 15 hours at room temperature.

The reaction is quenched with water and ethyl acetate is added. The layers are separated and the organic layer is washed with brine, dried over MgSO₄ and concentrated in vacuo to give an oil. The crude product is purified by dry column chromatography over silica gel eluting with a solvent system of ethyl acetate in methylene chloride to give methyl 4-phenyl-3-carboethoxyvinylphenylacetate which is confirmed by NMR and used directly in the next step.

Step B:
4-phenyl-3-[(N-methyl-N-phenethyl)carbamoylmethyl]phenylacetic acid

When methyl cis-3-carbomethoxyvinyl-4-benzyloxyphenylacetate in the procedure of Example 13, Step B is replaced by methyl 4-phenyl-3-carbomethoxyvinylphenylacetate, then the product obtained is 4-phenyl-3-[(N-methyl-N-phenethyl)carbamoylmethyl]phenylacetate, which is used directly in the next step.

Step C:
2-phenyl-5-[(N-methyl-N-phenethyl)carbamoylmethyl]carboethoxyvinylbenzene To a suspension of 2.53 g (8.16 mmoles) of methyl 4-phenyl-3-carboethoxyvinylphenylacetate in 75 ml CH₂Cl₂ is added 2.64 g (16.32 mmoles) of 1,1′-carbonyldiimadazole. After 20 minutes 1.19 ml (8.16 mmoles) of N-methyl-N-phenethylamine is added dropwise. After stirring for 4 hours, 261 mg (8.16 mmoles) of MeOH and 20 mg of 4-dimethylaminopyridine is added. The reaction mixture is stirred for 12 hours after which time it is concentrated down in vacuo. Purification by flash chromatography gives 2-phenyl-5-[(N-methyl-N-phenethyl)carbamoylmethyl]carboethoxyvinylbenzene. NMR confirms this structure which is used directly in the next step.

Step D:
2-phenyl-5-(N-methyl-N-phenethyl)carbamoylmethyl]carboxyvinylbenzene A solution of 1.61 g (3.92 mmoles) of 2-phenyl-5-[(N-methyl-N-phenethyl)carbamoylmethyl]carboethoxyvinylbenzene in 25 ml EtOH is added 8 ml of 1N NaOH. After 12 hours at 40° C., the reaction mixture is concentrated down in vacuo, taken up in H₂O and acidified to pH 3 with 1N HCl. The resulting precipitate is collected to give 2-phenyl-5-[(N-methyl-N-phenethyl)carbamoylmethyl]carboxyvinylbenzene.

EXAMPLE 16
2-(N-methyl-N-phenethyl)carbamoylmethyl-4-phenyl)-5-[2-methyl-2-(1H-tetrazol -5-yl)propoxy]pyridine

Step A:
2-carbomethoxymethyl-4-phenyl-5-(2-methyl-2-cyano)-propoxypyridine

To a solution of 2.18 g (9.0 mmoles) of 2-carbomethoxymethyl-4-phenyl-5-hydroxypyridine in 75 ml acetone is added 1.24 g (9.0 mmoles) of K₂CO₃ followed by 1.77 g (9.0 mmoles) of 2-methyl-2-cyanopropylbromide. This reaction mixture is refluxed for 2 hours, cooled to room temperature, filtered and concentrated down in vacuo. Purification by flash chromatography affords 2-carbomethoxymethyl-4-phenyl-5-(2-methyl-2-cyano)-propoxypyridine which is used directly in the next step.

Step B:
2-carboxymethyl-4-phenyl-5-(2-methyl-2-cyano)-propoxypyridine

When the procedure of Example 1, Step H is followed the ester of Step A is hydrolyzed to obtain 2-carboxymethyl-4-phenyl-5-(2-methyl-2-cyano)propoxypyridine.

Step C:
2-[(N-methyl-N-phenethyl)carbamoylmethyl]-4-phenyl-5-(2-methyl-2-cyano)propoxypyridine To a suspension of 2.53 g (8.16 mmoles) of 2-carbomethoxymethyl-4-phenyl-5-(2-methyl-2-cyano) propoxypyridine in 75 ml CH₂Cl₂ is added 2.64 g (16.32 mmoles) of 1,1′-carbonyldiimadazole. After 20 minutes 1.19 ml (8.16 mmoles) of N-methyl-N-phenethylamine is added dropwise. After stirring for 4 hours, 261 mg (8.16 mmoles) of MeOH and 20 mg of 4-dimethylaminopyridine is added. The reaction mixture is stirred for 12 hours after which time it is concentrated down in vacuo. Purification by flash chromatography gives 2-[(N-methyl-N-phenethyl)carbamoylmethyl]-4-phenyl-5-(2-methyl-2-cyano)propoxypyridine. NMR confirms this structure which is used directly in the next step.

Step D:
2-(N-methyl-N-phenethyl)carbamoylmethyl-4-phenyl)-5-[2-methyl-2-(1H-tetrazol-5-yl) propoxy]pyridine A mixture of 2-[(N-methyl-N-phenethyl)carbamoylmethyl]-4-phenyl-5-(2-methyl-2-cyano)propoxypyridine (0.85 g, 2 mmol), NaN₃ (1.2 g, 18 mmol), NH₄Cl (0.96 g, 18 mmol) and DMF (5 ml) is heated to 100° C. for 10 hours.

This is then poured into H₂O and extracted with ethyl acetate (2×25 ml). The ethyl acetate is dried (Na₂SO₄) and concentrated in vacuo. The oily residue is triturated in ethyl acetate to obtain 2-(N-methyl-N-phenethyl)carbamoylmethyl-4-phenyl)-5-[2-methyl-2-(1H-tetrazol-5-yl)propoxy]pyridine.

EXAMPLE 17

When the procedure of Example 16 is followed and 2-carbomethoxymethyl-4-phenyl-5-hydroxypyridine is replaced with 2-phenyl-5-(carbomethoxymethyl)phenol or 2-phenyl-4-(carbomethoxymethyl)phenol, then the products prepared are: N-methyl-N-phenethyl-2-[4-phenyl-3-(2-methyl-2-tetrazol-5-yl)propoxy]phenylacetamide and N-methyl-N-phenethyl-2-[3-phenyl-4-(2-methyl-2-tetrazol-5-yl)propoxy]phenylacetamide.

EXAMPLE 18
3′-benzyloxy-5′-[(N-methyl-N-phenethyl)carbamoylmethyl]-3-methylcinnamic acid Step A: Ethyl 3′,5′-di(benzyloxy)-3-methylcinnamate A solution of 3.58 ml (4.05 g, 18.05 mmol, 1.2 eq) of triethylphosphonoacetate and 0.54 g (18.05 mmol, 1.2 eq) of an 80% NaH oil dispersion in 20 ml of THF is stirred at 25° C. for 1¼ hours. To this is added 3,5-di(benzyloxy)phenyl methyl ketone 5.0 g 15.04 mmol) which is then stirred for 72 hours. The mixture is partitioned between EtOAc and H₂O. The organics are dried (MgSO₄) and concentrated in vacuo to give ethyl 3′,5′-di(benzyloxy)-3-methylcinnamate which is confirmed by NMR and used directly in the next step.

Step B: Ethyl 3′-hydroxy-5′-benzyloxy-3-methylcinnamate

To a solution of 3.7 g (9.24 mmol) of ethyl 3′,5′-di(benzyloxy)-3-methylcinnamate in 50 ml of CH₂Cl₂ at 0° C. is added 1.97 ml (9.24 mmol) of 30% HBr in HOAc. This is stirred at 0° C. for 1 hour, then at 25° C. for 18 hours. The mixture is concentrated in vacuo and partitioned between EtOAc and H₂O. The organics are dried (MgSO₄) and concentrated in vacuo. purification by flash silica gel chromatography using 10% EtOAc in hexanes as an eluent affords 0.775 g of ethyl 3′-hydroxy-5′-benzyloxy-3-methylcinnamate in the form of a clear oil that crystallizes upon sitting. NMR confirms this structure and is used directly in the next step.

Step C: Ethyl 3′-trifluorosulfonyloxy-5′-benzyloxy-3-methylcinnamate

To a solution of 0.77 g (2.47 mmol) of ethyl 3′-hydroxy-5′-benzyloxy-3-methylcinnamate in 20 ml of pyridine at 0° C. is added 0.50 ml (0.83 g, 2.96 mmol, 1.2 eq) of trifluoromethanesulfonic anhydride. This is stirred at 0° C. for ½ an hour followed by 18 hours at 25° C. The mixture is partitioned between EtOAc and 1N HCl. The organics are dried (MgSO4) and concentrated in vacuo. purification by flash silica gel chromatography using $CH_2Cl_2$ as an eluent affords ethyl 3'-trifluorosulfonyloxy-5'-benzyloxy-3-methylcinnamate in the form of a clear oil which is confirmed by NMR and used directly in the next step.

Step D: Ethyl 3'-vinyl-5'-benzyloxy-3-methylcinnamate

A solution of 0.5 g (1.13 mmol) ethyl 3'-trifluorosulfonyloxy-5'-benzyloxy-3-methylcinnamate, 0.016 g (0.023 mmol, 0.02 eq) of bis-triphenylphosphinepalladium II chloride, 0.14 g (3.38 mmol, 3 eq) of LiCl and 0.38 g (1.18 mmol, 1.05 eq) of vinyltributyltin in 20 ml of DMF are stirred at 25° C. for 72 hours. The mixture is partitioned between EtOAc and $H_2O$. The organics are dried (MgSO4) and concentrated in vacuo. Purification by flash silica gel chromatography using 7% EtOAc in hexanes affords ethyl 3'-vinyl-5'-benzyloxy-3-methylcinnamate in the form of a clear oil which is confirmed by NMR and used directly in the next step.

Step E: Ethyl 3'-hydroxyethyl-5'-benzyloxy-3-methylcinnamate

A solution of 0.43 g (1.3 mmol) ethyl 3'-vinyl-5'-benzyloxy-3-methylcinnamate and 0.88 ml (0.88 mmol, 0.66 eq, 2 hydride eq) of 1.0M $BH_3$·THF complex in 15 ml of THF under argon is stirred at 25° C. for 2 hours. To this is added 2.6 ml of $H_2O$, 2.6 ml of 1N NaOH and 4.0 ml of 30% $H_2O_2$ which then is stirred for 1½ hours. This is acidified to pH~1 using 1N HCl and partitioned between EtOAc and $H_2O$. The organics are dried (MgSO4) and concentrated in vacuo. Purification by flash silica gel chromatography using 20% EtOAc in hexanes as an eluent affords ethyl 3'-hydroxyethyl-5'-benzyloxy-3-methylcinnamate in the form of a clear oil which is confirmed by NMR and used directly in the next step.

Step F: Ethyl 3'-carboxymethyl-5'-benzyloxy-3-methylcinnamate

A solution of 0.225 g (0.66 mmol) ethyl 3'-hydroxyethyl-5'-benzyloxy-3-methylcinnamate and 0.6 ml (1.98 mmol, 3 eq) of 3.3M Jones reagent in 10 ml of acetone is stirred at 0° C. for ½ an hour. The mixture is partitioned between EtOAc and $H_2O$. The organics are dried (MgSO4) and concentrated in vacuo to afford ethyl 3'-carboxymethyl-5'-benzyloxy-3-methylcinnamate in the form of a yellow oil which is confirmed by NMR and used directly in the next step.

Step G: Ethyl 3'-(N-methyl-N-phenethyl)carbamoyl-methyl]-5'-benzyloxy-3-methylcinnamate A solution of 0.23 g (0.649 mmol) of ethyl 3'-carboxymethyl-5'-benzyloxy-3-methylcinnamate, 0.12 g (0.714 mmol, 1.1 eq) of carbonyldiimidazole and a catalytic amount of DMAP in 15 ml of $CH_2Cl_2$ is stirred at 25° C. for ½ an hour. To this is added 0.104 ml (0.097 g, 0.714 mmol, 1.1 eq) of N-methyl-N-phenethylamine which is then stirred for 18 hours. The mixture is concentrated in vacuo and partitioned between EtOAc and 1N HCl. The organics are dried (MgSO4) and concentrated in vacuo. Purification by preparative thick layer chromatography developed in 40% EtOAc in hexanes affords ethyl 3'-[(N-methyl-N-phenethyl)carbamoylmethyl]-5'-benzyloxy-3-methylcinnamate in the form of a clear oil which is confirmed by NMR and IR and used directly in the next step.

Step H: 3'-N-methyl-N-phenethyl)carbamoylmethyl]-5'-benzyloxy-3-methylcinnamic acid A solution of 0.22 g (0.47 mmol) ethyl 3'-[(N-methyl-N-phenethyl)carbamoylmethyl]-5'-benzyloxy-3-methylcinnamate and 0.097 g (2.33 mmol, 5 eq) of LiOH·H2O in 15 ml of 1:1:1 —THF:EtOH:H2O is stirred at 25° C. for 18 hours. The mixture is partitioned between $Et_2O$ and $H_2O$. The aqueous layer is acidified to pH~1 using 1N HCl and extracted with EtOAc. The organics are dried (MgSO4) and concentrated in vacuo. Purification by preparative thick layer chromatography developed in 5% MeOH in $CH_2Cl_2$ affords 3'-[N-methyl-N-phenethyl)carbamoylmethyl]-5'-benzyloxy-3-methylcinnamic acid in the form of a white oil. This is confirmed by NMR and IR.

Calc'd: C, 75.82; H, 6.59; N, 3.16;
Found: C, 72.86; H, 6.58; N, 3.04.

EXAMPLE 19

When triethylphosphonoacetate in the procedure of Example 18 is replaced with the phosphonates of Table I below and 3,5-di(benzyloxy)phenylmethylketone is replaced by the various aldehydes and ketones of this invention then the corresponding product is prepared.

TABLE I trimethylphosphonoacetate
triethylphosphono-2-propionate
triethylphosphono-3-butanoate
triethylphosphono-4-buten-2-oate
triethylphosphono-2-butanoate

EXAMPLE 20

When 2-phenyl-5-carbomethoxymethylbenzaldehyde in the procedure of Example 15 is replaced with 2-phenoxy-5-carbomethoxymethylbenzaldehyde, then the product obtained is 2-phenoxy-5-[(N-methyl-N-phenethyl)carbamoylmethyl]carboxyvinylbenzene.

EXAMPLE 21

N-methyl-N-phenethyl-2-(5-benzyloxy-2-carboxyphenyl)acetamide

Step A: N-methyl-N-phenethyl-2-(3-benzyloxyphenyl)acetamide

When ethyl 3'-carboxymethyl-5'-benzyloxy-3-methylcinnamate in the procedure of Example 18, Step G is replaced with 3-benzyloxyphenylacetic acid, then the product obtained is N-methyl-N-phenethyl-2-(3-benzyloxyphenyl)acetamide.

Step B: N-methyl-N-phenethyl-2-(5-benzyloxy-2-formylphenyl)acetamide

Phosphorus oxychloride (1.61 ml, 0.0173 mol) is added dropwise to 1.34 ml of N,N-dimethylformamide (DMF) while the reaction mixture is maintained between 10° to 20° C. with an external cooling bath. A solution of N-methyl-N-phenethyl-2-(3-benzyloxyphenyl)acetamide (3.73 g, 0.0144 mol) in DMF is added dropwise, the resulting mixture is heated at 100° C. for 6 hours. After cooling to room temperature, the reaction mixture is poured into an ice/H₂O mixture, ethyl acetate is added, followed by 7.3 g of sodium acetate. The resulting mixture is stirred for 1 hour. The layers are separated. The organic layer is washed with 10 ml of 1N aqueous HCl and brine; dried (MgSO₄) and concentrated concentrated in vacuo. The residue obtained is purified by a flash column packed with silica gel and eluted with 5% ethyl acetate in CH₂Cl₂ to give N-methyl-N-phenethyl-2-(5-benzyloxy-2-formylphenyl)acetamide. NMR confirms this structure.

Step C:
N-methyl-N-phenethyl-2-(5-benzyloxy-2-carboxyphenyl)acetamide

When ethyl 3'-hydroxyethyl-5'-benzyloxy-3-methylcinnamate in Example 18, Step F is replaced with N-methyl-N-phenethyl -2-(5-benzyloxy-2-formylphenyl)acetamide, then the product obtained is N-methyl-N-phenethyl-2-(5-benzyloxy-2-carboxyphenyl)acetamide.

EXAMPLE 22
N-methyl-N-phenethyl-2-5-benzyloxy-2-(2-carboxyvinyl)phenyl]acetamide

Step A:
N-methyl-N-phenethyl-2-[5-benzyloxy-2-(2-carboethoxyvinyl)phenyl]acetamide When 2-phenyl-5-carbomethoxymethylbenzaldehyde in the procedure of Example 15, Step A is replaced with N-methyl-N-phenethyl-2-(5-benzyloxy-2-formylphenyl)acetamide, then the product obtained is N-methyl-N-phenethyl-2-[5-benzyloxy-2-(2-carboethoxyvinyl)phenyl]acetamide. NMR confirms this structure.

Step B:
N-methyl-N-phenethyl-2-[5-benzyloxy-2-(2-carboxyvinyl)phenyl]acetamide Following the procedure of Example 1, Step J, N-methyl-N-phenethyl-2-[5-benzyloxy-2-(2-carboethoxyvinyl)phenyl]acetamide is hydrolyzed to N-methyl-N-phenethyl-2-[5-benzyloxy-2-(2-carboxyvinyl)phenyl]acetamide.

EXAMPLE 23

When triethylphosphonoacetate in the procedure of Example 22 is replaced with the phosphonates of Table I, then the corresponding products are prepared.

EXAMPLE 24

When N-methyl-N-phenethyl-2-(5-benzyloxy-2-formylphenyl)acetamide in the procedure of Example 22 is replaced with N-methyl-N-phenethyl-2-(4-benzyloxy-2-formylphenyl)acetamide, N-methyl-N-phenethyl-2-(5-phenyl-2-formylphenyl)acetamide and N-methyl-N-phenethyl-2-(5-phenoxy-2-formylphenyl)acetamide, then the corresponding products are obtained.

We claim:
1. A compound having selective LTB₄ antagonist properties of the formula

[Structure: central benzene ring with substituents E—(C)ₑ—D—(C)_d, G—(C)_g—F—(C)_f, (R₁)₀₋₂, and —A—(C)_a—C(=O)—N(R')—(C)_b—B with R groups on carbons]

where $$-A-(C)_a-\overset{O}{\underset{R}{C}}-\overset{R'}{\underset{}{N}}-(C)_b-B \text{ is selected from}$$

$$-CH_2-\overset{O}{C}-\overset{R'}{\underset{}{N}}-CH_2CH_2-\underset{}{\bigcirc}-R'' \text{ and}$$

$$-O-CH_2-\overset{O}{C}-\overset{R'}{\underset{}{N}}-CH_2CH_2-\underset{}{\bigcirc}-R''$$

where R' is hydrogen or lower alkyl and R'' is hydrogen, lower alkyl or lower alkoxy;

$$-(C)_d-D-(C)_e-E$$
(with R groups on carbons)

is selected from —(CRR)_d—E where d is 0–4, —(CR=CR)_x—E where x is 1-2 —O—(CRR)_d—E where d is 1–3, and —O—(CRR)_d—CR=CR—E where d is 1–3 and where R is hydrogen or loweralkyl and E is —COOH or

[tetrazole structure]

$$-(C)_l-F-(C)_g-G \text{ is selected from}$$

$$-(CRR)_g-\underset{}{\bigcirc}-R'' \text{ and}$$

$$-O-(CRR)_g-\underset{}{\bigcirc}-R''$$

where g is 0–3, R is hydrogen or lower alkyl and R'' is hydrogen, lower alkyl or lower alkoxy; and R₁ is hydrogen, alkyl, alkenyl, phenyl, alkoxy, amino, mono- and di-alkylamino, mercapto, alkylthio, halo or haloalkyl; or a pharmaceutically acceptable salt thereof.

2. A compound according to claim 1 of the formula:

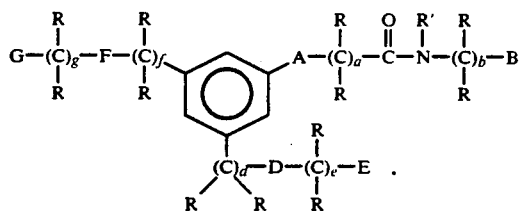

3. A compound according to claim 1 of the formula:

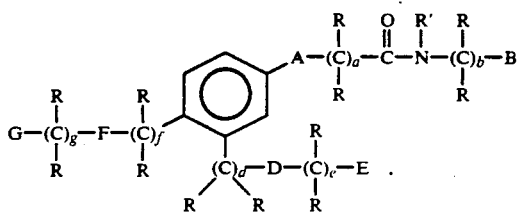

4. A compound according to claim 2 which is 3-[(N-methyl-N-phenethyl)carbamoylmethyl]-5-benzyloxy-β-methylcinnamic acid or a pharmaceutically acceptable salt thereof.

5. A compound according to claim 3 which is trans-N-methyl-N-phenethyl-2-[4-benzyloxy-3-(2-carboxyvinyl)-phenyl]acetamide or a pharmaceutically acceptable salt thereof.

6. A compound according to claim 3 which is cis-N-methyl-N-phenethyl-2-[4-benzyloxy-3-(2-carboxyvinyl)phenyl]acetamide or a pharmaceutically acceptable salt thereof.

7. N-methyl-N-phenethyl-2-[5-benzyloxy-2-(2-carboxyvinyl)phenyl]acetamide or a pharmaceutically acceptable salt thereof.

8. 2-phenoxy-5-[(N-methyl-N-phenethyl)carbamoylmethyl]carboxyvinylbenzene or a pharmaceutically acceptable salt thereof.

9. A method for the treatment of hypersensitive ailments in humans and mammals comprising administering thereto an effective amount of a compound of the formula according to claim 1.

10. A method for the treat of inflammatory diseases in humans and mammals comprising administering thereto an effective amount of a compound of the formula according to claim 1.

11. A method according to claim 10 where the inflammatory disease is inflammatory bowel disase.

12. A pharmaceutical composition where the active ingredient is a compound according to claim 1 in admixture with a pharmaceutical carrier.

* * * * *